United States Patent [19]
Elliott et al.

[11] Patent Number: 4,871,389
[45] Date of Patent: Oct. 3, 1989

[54] HETEROCYCLIC COMPOUNDS

[75] Inventors: Raymond Elliott, Nr Reading; Raymond Sunley, Twyford; David A. Griffin, Bracknell, all of England

[73] Assignee: Imperial Chemical Industries PLC, London, England

[21] Appl. No.: 853,915

[22] Filed: Apr. 21, 1986

[30] Foreign Application Priority Data

May 3, 1985 [GB] United Kingdom ............... 8511344

[51] Int. Cl.$^4$ ............... A01N 43/653; C07D 249/12
[52] U.S. Cl. ............................... 71/92; 71/76; 548/101; 548/262; 548/341
[58] Field of Search ............ 548/262, 101; 71/92, 71/76

[56] References Cited

U.S. PATENT DOCUMENTS

| | | | |
|---|---|---|---|
| 4,243,405 | 1/1981 | Balasubramanyan et al. | 548/262 |
| 4,414,210 | 11/1983 | Miller et al. | 514/383 |
| 4,436,548 | 3/1984 | Zeeh et al. | 71/76 |
| 4,472,415 | 9/1984 | Worthington | 548/262 |
| 4,496,388 | 1/1985 | Clough | 548/262 |
| 4,507,140 | 3/1985 | Sugavanam | 548/262 |
| 4,532,234 | 7/1985 | Buschmann et al. | 514/63 |
| 4,554,285 | 11/1985 | Zeeh et al. | 514/383 |
| 4,578,396 | 3/1986 | Jager et al. | 548/262 |
| 4,659,705 | 4/1987 | Zeeh et al. | 514/184 |
| 4,689,337 | 8/1987 | Bushell et al. | 514/383 |

FOREIGN PATENT DOCUMENTS

| | | |
|---|---|---|
| 0049913 | 4/1982 | European Pat. Off. |
| 0061835 | 6/1982 | European Pat. Off. |
| 0077479 | 4/1983 | European Pat. Off. ............ 548/262 |
| 0078594 | 5/1983 | European Pat. Off. ............ 548/262 |
| 0082400 | 6/1983 | European Pat. Off. ............ 548/262 |
| 0084597 | 8/1983 | European Pat. Off. ............ 548/262 |
| 0096786 | 12/1983 | European Pat. Off. ............ 548/262 |
| 0097425 | 1/1984 | European Pat. Off. ............ 548/262 |
| 0099165A1 | 1/1984 | European Pat. Off. ............ 548/262 |
| 0129798 | 2/1985 | European Pat. Off. |
| 0158448 | 10/1985 | European Pat. Off. |
| 0183494 | 4/1986 | European Pat. Off. |
| 0232889 | 8/1987 | European Pat. Off. |
| 1425288 | 2/1976 | United Kingdom ............... 548/262 |
| 1529818 | 10/1978 | United Kingdom ............... 548/262 |
| 2120235A | 4/1983 | United Kingdom ............... 548/261 |
| 2196991A | 1/1984 | United Kingdom ............... 548/341 |

OTHER PUBLICATIONS

EP 113644A (Abstract) Ciba-Geigy.
EP 91,398A (Abstract) Mueller et al.
DE 2926-096 (Abstract) Zeeh et al.
DE 3222-166A (Abstract) Bayer et al.

*Primary Examiner*—Richard L. Raymond
*Assistant Examiner*—Patricia L. Morris
*Attorney, Agent, or Firm*—Cushman, Darby & Cushman

[57] ABSTRACT

A compound having the general formula:

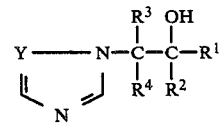

and stereoisomers thereof, wherein $R^1$ is alkyl, alkenyl, alkynyl, cycloalkyl or cycloalkenyl, all having up to 8 carbon atoms; or is aryl, aralkyl or heterocyclyl, any of which may be optionally substituted; $R^2$ is alkyl, alkenyl, alkynyl, alkynylalkenyl, alkenyl alkynyl, cycloalkyl, cycloalkenyl, or cycloalkylalkyl, all of which contain up to 8 carbon atoms and may be substituted; $R^3$ and $R^4$, which can be the same or different, are hydrogen (but are not both hydrogen) or are alkyl of up to 4 carbon atoms, alkoxy of up to 4 carbon atoms, $OCF_3$, $CF_3$ or halogen, or together constitute a ring of 3–6 carbon atoms; and Y is =CH— or =N—; and esters, ethers, salts and metal complexes thereof. The compounds are useful as plant growth regulating agents.

6 Claims, No Drawings

HETEROCYCLIC COMPOUNDS

This invention relates to heterocyclic compounds useful as plant growth regulating agents, to processes for preparing them, to compositions containing them, and to methods of regulating plant growth using them.

The invention provides compounds having the general formula (I):

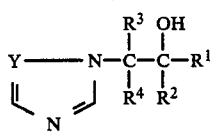
(I)

and stereoisomers thereof, wherein $R^1$ is alkyl, alkenyl, alkynyl, cycloalkyl, or cycloalkenyl, all having up to 8 carbon atoms; or is aryl, aralkyl or heterocyclyl, any of which may be optionally substituted; $R_2$ is alkyl, alkenyl, alkynyl, alkynylalkenyl, alkenylalkynyl, cycloalkyl, cycloalkenyl, or cycloalkylalkyl, all of which contain up to 8 carbon atoms and may be substituted; $R^3$ and $R^4$, which can be the same or are different, are hydrogen (but are not both hydrogen) or are alkyl of up to 4 carbon atoms, alkoxy of up to 4 carbon atoms, $OCF_3$, $CF_3$ or halogen or together constitute a ring of 3–6 atoms; and Y is =CH— or =N—; and esters, ethers, salts and metal complexes thereof.

The compounds of the invention may contain chiral centres. Such compounds are generally obtained in the form of racemic mixtures. However, these and other mixtures can be separated into the individual isomers by methods known in the art, and this invention embraces such isomers.

Preferred alkyl groups for $R^1$ and $R^2$ contain from 1 to 8, especially 3 to 7 carbon atoms. When $R^1$ and $R^2$ are alkyl they can be a straight or branched chain alkyl groups, examples being methyl, ethyl, propyl (n- or iso-propyl) and butyl (n-, sec-, iso-or t-butyl), amyl and hexyl; $R^1$ and $R^2$ when alkyl may be substituted with one or more halogens.

Preferred alkyl groups for $R^1$ are i-propyl and especially t-butyl, and these may be substituted with one or more halogen atoms, eg. fluorine or chlorine.

Preferred alkyl groups for $R^3$ and $R^4$ contain up to 4 carbon atoms and are preferably, for example, methyl or ethyl.

Preferred cycloalkyl groups are cyclopropyl, cyclobutyl, cyclopentyl, and cyclohexyl, and these may be substituted by alkyl groups. Cyclopropyl and methylcylopropyl are preferred. Preferred cycloalkylalkyl groups are cycloalkylmethyl or cycloalkylethyl groups. Preferred alkenyl and alkynyl groups for $R^1$ and $R^2$ contain up to 8 carbon atoms, especially from 3 to 7 carbon atoms and include allyl and propargyl.

When $R^1$ is aryl, eg. phenyl, it may be unsubstituted, or substituted with 1,2 or 3 ring substituents, which may be the same or different. Example of suitable ring substituents which may be carried on the aryl group include halogen, for example fluorine, chlorine or bromine, $C_1$ to $C_4$ alkyl and $C_1$ to $C_4$ alkoxy. Examples of aryl groups for $R^1$ are phenyl, 2-, 3-, or 4-chlorophenyl, 2,4- or 2,6-dichlorophenyl, 2,4- or 2,6-difluorophenyl, 2-, 3- or 4-fluorophenyl, 2-, 3- or 4-bromophenyl, 2-, 3- or 4-methoxyphenyl, 2,4-dimethoxyphenyl, 2-, 3- or 4-ethoxyphenyl, 2-fluoro-4-chlorophenyl, 2-chloro-4-fluorophenyl, 2-, 3- or 4-methylphenyl, 2-, 3- or 4-ethylphenyl, 2-, 3- or 4-trifluoromethylphenyl, 4-phenylphenyl (4-biphenylyl), 2-chloro-4-methoxyphenyl), 2-fluoro-4-methoxyphenyl, 2-methoxy-4-fluorophenyl, 2-methoxy-4-chlorophenyl, 2-chloro-4-methylphenyl, 2-fluoro-4-methylphenyl, 4-isopropylphenyl.

When $R^1$ is heteroaryl (ie. heteroaromatic), it may be, for example, a thiophene, furan or pyridine group, which may be unsubstituted or substituted. Suitable substituents include for example those defined above for the aryl, eg. phenyl moiety of $R^1$.

$R^2$ is preferably alkyl, alkenyl, alkynyl, alkynylalkenyl, alkenylalkynyl, cycloalkyl, cycloalkenyl, cycloalkylalkyl, all of which contain from 4 to 8 carbon atoms and may be substituted by one or more substituents. As examples of suitable substituents there may be mentioned halogen, for example fluorine, chlorine and bromine; hydroxy; $C_1$ to $C_2$ alkoxy; tri-($C_1$- to $C_4$)alkyl silyl, for example trimethyl or triethyl silyl; ($C_1$ to $C_4$ alkoxy) carbonyl; and the oxime group and ether derivatives thereof.

Especially preferred values for $R^2$ are —($CH_2$)$_n$—C≡CX, —($CH_2$)$_n$—C(T)=C(T)X or —($CH_2$)$_m$—X where X is $C_2H_5$, —$C_3H_7$, $C_4H_9$, —$C_5H_{11}$, —C≡C$C_2H_5$, —CH=CH—$C_2H_5$, —CH=C($CH_3$)$_2$, —$CH_2$CH=$CH_2$, —$CH_2$C≡C$CH_3$, —$CH_2$CH= CH—$CH_3$, —C≡C—$C_3H_7$, —CH=CH—$C_3H_7$, —($CH_2$)$_2$$CF_3$, —($CH_2$)$_3$, —$CF_3$, —($CF_2$)$_2$$CF_3$, —($CF_2$)$_3$$CF_3$,

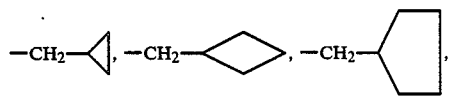

—$CH_2$C≡C$C_3H_7$, —$CH_2$CH=CH$C_3H_7$, —$CH_2$OH, —$CH_2$O$CH_3$, —$CH_2$O$C_2H_5$, —$CH_2$O$C_3H_7$, —$CH_2$O$C_4H_9$, —($CH_2$)$_3$Cl, —($CH_3$)$_2$O$CH_3$, —CH(O$C_2H_5$)$_2$, —COO$C_2H_5$, —CH=NOH, —CH=NO$CH_2$$C_6H_5$, —Si($CH_3$)$_3$; (T) is hydrogen or a halogen atom, for example fluorine, chlorine orbromine; and n is from 0 to 3 (preferably 0 or 1) and m is from 0 to 5 (preferably from 0 to 3), provided that the total number of carbon atoms in the group $R^2$ is from 4 to 8.

More especially preferred values for $R^2$ are —C≡CX, —CH=CHX or $CH_2CH_2$X wherein X is an alkyl group containing from 3 to 5 carbon atoms ie. —$C_3H_7$ (n- or iso- propyl), —$C_4H_9$ (n-, sec-, iso- or t-butyl) or $C_5H_{11}$ (straight or branched chain pentyl).

Preferred values for $R^3$ and $R^4$, which may be the same or different, are H, $CH_3$, $OCH_3$, $OCF_3$, $C_2H_5$, $C_3H_7$, $CF_3$, F or Cl, and especially H, $CH_3$ or $C_2H_5$, provided $R^3$ and $R^4$ are not both hydrogen.

When $R^3$ and $R^4$ together form a bridging group it is preferably —$CH_2$—$CH_2$—, —($CH_2$)$_3$— or —($CH_2$)$_4$—.

Y is preferably =N—, ie. triazoles are preferred to imidazoles.

The present invention includes salts, ethers, esters and metal complexes, of the above defined compounds. Preferred salts are acid addition salts. Useful ethers are preferably simple alkyl, alkenyl, alkynyl, aryl or aralkyl ethers eg. methyl, ethyl, propyl, butyl, allyl, propargyl, phenyl or benzyl ethers whilst the esters may be, for example acetates, or benzoates. Without limitation of the generality of the above statement, the present invention also includes any compound which breaksdown in agrochemical use to form a compound of formula (I).

Examples of the compounds of the invention are shown in Table I below in which the different values for $R^1$, $R^2$, $R^3$ and Y in the general formula.

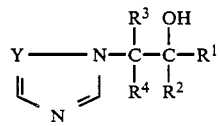

are presented.

TABLE I

| NO. | $R_1$ | $R_2$ | $R_3$ | $R_4$ | Y | M.pt. (°C.) | COMMENTS |
|---|---|---|---|---|---|---|---|
| 1 | $^tBu$ | $-C{\equiv}C(CH_2)_3CH_3$ | H | $CH_3$ | N | 90-92 | isomer A |
| 2 | $^tBu$ | $-C{\equiv}C(CH_2)_3CH_3$ | H | $CH_3$ | N | Oil | isomer B |
| 3 | $^tBu$ | $-C{\equiv}C(CH_2)_2CH_3$ | H | $CH_3$ | N | 76-78 | isomer A |
| 4 | $^tBu$ | $-C{\equiv}C(CH_2)_2CH_3$ | H | $CH_3$ | N | 110-112 | isomer B |
| 5 | $^tBu$ | $-C{\equiv}CCH(CH_3)_2$ | H | $CH_3$ | N | 101-102 | 89:11 mixture of isomers |
| 6 | $^tBu$ | $-C{\equiv}C(CH_2)_2CH_3$ | $CH_3$ | $CH_3$ | N | 73.5-73.5 | |
| 7 | $^tBu$ | $-C{\equiv}CCH(CH_3)_2$ | H | $C_2H_5$ | N | 129-131.5 | single isomer |
| 8 | $^tBu$ | $-C{\equiv}C(CH_2)_2CH_3$ | H | $C_2H_5$ | N | 99-101 | 98:2 mixture of isomers |
| 9 | $^tBu$ | $-C-C{\equiv}C(CH_2)_4CH_3$ | H | $CH_3$ | N | | |
| 10 | $^tBu$ | $-C-C{\equiv}C(CH_2)_3CH_3$ | H | $C_2H_5$ | N | 80-81.5 | |
| 11 | $^tBu$ | $-C-C{\equiv}C(CH_2)_3CH_3$ | $CH_3$ | $CH_3$ | N | | |
| 12 | $^tBu$ | $-C-C{\equiv}CC_2H_5$ | $CH_3$ | $CH_3$ | N | | |
| 13 | $^tBu$ | $-C-C{\equiv}CCH(CH_3)_2$ | $CH_3$ | $CH_3$ | N | 83.7-85.4 | |
| 14 | $^tBu$ | $-C{\equiv}CCH(CH_3)C_2H_5$ | H | $CH_3$ | N | 105.5-107 | |
| 15 | $^tBu$ | $-C{\equiv}CCH(CH_3)C_2H_5$ | H | $C_2H_5$ | N | 108-110 | |
| 16 | $^tBu$ | $-C{\equiv}CCH(CH_3)C_2H_5$ | $CH_3$ | $CH_3$ | N | | |
| 17 | $^tBu$ | $-C{\equiv}CCH_2CH(CH_3)_2$ | H | $CH_3$ | N | 87.5-89 | |
| 18 | $^tBu$ | $-C{\equiv}CCH_2CH(CH_3)_2$ | H | $C_2H_5$ | N | 80-83 | |
| 19 | $^tBu$ | $-C{\equiv}CCH_2CH(CH_3)_2$ | $CH_3$ | $CH_3$ | N | 70-71 | |
| 20 | $^tBu$ | $-C{\equiv}C(CH_2)_4CH_3$ | H | $CH_3$ | N | | |
| 21 | $^tBu$ | $-C{\equiv}C(CH_2)_4CH_3$ | H | $C_2H_5$ | N | | |
| 22 | $^tBu$ | $-C{\equiv}C(CH_2)_4CH_3$ | $CH_3$ | $CH_3$ | N | | |
| 22A | $^tBu$ | $-C{\equiv}C(CH_2)_2CH(CH_3)_2$ | H | $CH_3$ | N | 96-99 | isomer A |
| 23B | $^tBu$ | $-C{\equiv}C(CH_2)_2CH(CH_3)_2$ | H | $CH_3$ | N | Oil | isomer B |
| 24 | $^tBu$ | $-C{\equiv}C(CH_2)_2CH(CH_3)_2$ | H | $C_2H_5$ | N | | |
| 25 | $^tBu$ | $-C{\equiv}C(CH_2)_2CH(CH_3)_2$ | $CH_3$ | $CH_3$ | N | | |
| 26 | $^tBu$ | $-C{\equiv}CCH_2CH(CH_3)C_2H_5$ | H | $CH_3$ | N | 75-77.5 | |
| 27 | $^tBu$ | $-C{\equiv}CCH_2CH(CH_3)C_2H_5$ | H | $C_2H_5$ | N | | |
| 28 | $^tBu$ | $-C{\equiv}CCH_2CH(CH_3)C_2H_5$ | $CH_3$ | $CH_3$ | N | | |
| 29 | $^tBu$ | $-C{\equiv}CCH(CH_3)CH_2CH_3$ | H | $CH_3$ | N | 85.5-88 | |
| 30 | $^tBu$ | $-C{\equiv}CCH(CH_3)CH_2CH_2CH_3$ | H | $C_2H_5$ | N | | |
| 31 | $^tBu$ | $-C{\equiv}CCH_2CH{=}CH_2$ | H | $CH_3$ | N | | |
| 32 | $^tBu$ | $-C{\equiv}CCH_2CH{=}CH_2$ | H | $C_2H_5$ | N | | |
| 33 | $^tBu$ | $-C{\equiv}CCH_2CH{=}CHCH_3$ | H | $CH_3$ | N | | |
| 34 | $^tBu$ | $-C{\equiv}CCH{=}CHC_2H_5$ | H | $CH_3$ | N | | |
| 35 | $^tBu$ | $-C{\equiv}CCH_2OC_2H_5$ | H | $CH_3$ | N | | |
| 36 | $^tBu$ | $-C{\equiv}CCH_2OCH_2CH_2CH_3$ | H | $CH_3$ | N | | |
| 37 | $^tBu$ | $-C{\equiv}C(CH_2)_3CH_3$ | H | $CH_3$ | N | | |
| 38 | $^tBu$ | $-C{\equiv}C(CH_2)_2CF_3$ | H | $CH_3$ | N | | |
| 39 | $^tBu$ | $-C{\equiv}C(CF_2)_3CF_3$ | H | $CH_3$ | N | | |
| 40 | $^tBu$ | $-CH{=}CH(CH_2)_3CH_3$ | H | $CH_3$ | N | 95.5-97.5 | cis |
| 41 | $^tBu$ | $-CH{=}CH(CH_2)_3CH_3$ | H | $CH_3$ | N | 44.5-48.5 | trans |
| 42 | $^tBu$ | $-CH{=}CH(CH_2)_2CH_3$ | H | $CH_3$ | N | | cis |
| 43 | $^tBu$ | $-CH{=}CH(CH_2)_2CH_3$ | H | $CH_3$ | N | | trans |
| 44 | $^tBu$ | $-CH{=}CH(CH_2)_2CH_3$ | H | $C_2H_5$ | N | | cis |
| 45 | $^tBu$ | $-CH{=}CH(CH_2)_2CH_3$ | H | $C_2H_5$ | N | 56-58.5 | trans |
| 46 | $^tBu$ | $-CH{=}CH(CH_2)_3CH_3$ | H | $C_2H_5$ | N | oil | cis |
| 47 | $^tBu$ | $-CH{=}CH(CH_2)_3CH_3$ | H | $C_2H_5$ | N | gum | trans |
| 48A | $^tBu$ | $-(CH_2)_4CH_3$ | H | $CH_3$ | N | | |
| 48B | $^tBu$ | $-(CH_2)_4CH_3$ | H | $CH_3$ | N | | isomer A |
| 49 | $^tBu$ | $-(CH_2)_4CH_3$ | H | $C_2H_5$ | N | | isomer B |
| 50 | $^tBu$ | $-(CH_2)_4CH_3$ | $CH_3$ | $CH_3$ | N | | |
| 51A | $^tBu$ | $-(CH_2)_5CH_3$ | H | $CH_3$ | N | oil | isomer A |
| 51B | $^tBu$ | $-(CH_2)_5CH_3$ | H | $CH_3$ | N | oil | isomer B |
| 52 | $^tBu$ | $-(CH_2)_5CH_3$ | H | $C_2H_5$ | N | 75-78 | |
| 53 | $^tBu$ | $-(CH_2)_5CH_3$ | $CH_3$ | $CH_3$ | N | | |
| 54 | $^tBu$ | $-C-C{\equiv}C(CH_2)_3CH_3$ | H | $OCH_3$ | N | | |
| 55 | $^tBu$ | $-C-C{\equiv}C(CH_2)_4CH_3$ | H | $OCH_3$ | N | | |
| 56 | $^tBu$ | $-CH{=}CH(CH_2)_3CH_3$ | H | $OCH_3$ | N | | cis |
| 57 | $^tBu$ | $-CH{=}CH(CH_2)_3CH_3$ | H | $OCH_3$ | N | | trans |
| 58 | $^tBu$ | $-(CH_2)_5CH_3$ | H | $OCH_3$ | N | | |
| 59 | $^tBu$ | $-(CH_2)_4CH_3$ | H | $OCH_3$ | N | | |
| 60 | $^tBu$ | $-C{\equiv}C(CH_2)_3CH_3$ | H | $CF_3$ | N | | |
| 61 | $^tBu$ | $-C{\equiv}C(CH_2)_4CH_3$ | H | $CF_3$ | N | | |
| 62 | $^tBu$ | $-(CH_2)_5CH_3$ | H | $CF_3$ | N | | |
| 63 | $^tBu$ | $-(CH_2)_4CH_3$ | H | $CF_3$ | N | | |
| 64 | $^tBu$ | $-C{=}C(CH_2)_3CH_3$ | F | F | N | | |
| 65 | $^tBu$ | $-(CH_2)_5CH_3$ | F | F | N | | |

TABLE I-continued

| NO. | $R_1$ | $R_2$ | $R_3$ | $R_4$ | Y | M.pt. (°C.) | COMMENTS |
|---|---|---|---|---|---|---|---|
| 66 | $^tBu$ | $-(CH_2)_4CH_3$ | F | F | N | | |
| 67 | $^tBu$ | 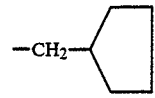 $-CH_2-$ | H | $CH_3$ | N | gum | 2:1 mixture of isomer |
| 68 | $^tBu$ | 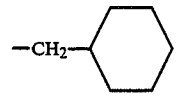 $-CH_2-$ | H | $CH_3$ | N | | |
| 69 | 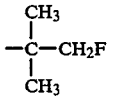 | $-C\equiv C(CH_2)_4CH_3$ | H | $CH_3$ | N | | |
| 70A | 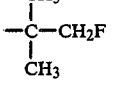 | $-C\equiv C(CH_2)_3CH_3$ | H | $CH_3$ | N | 72–74 | isomer A |
| 70B | 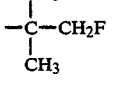 | $-C\equiv C(CCH_2)CH_3$ | H | $CH_3$ | N | gum | 1:1 mixture of isomers |
| 71 | 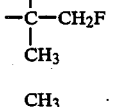 | $-(CH_2)_4CH_3$ | H | $CH_3$ | N | | |
| 72 | 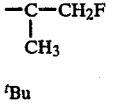 | $-(CH_2)_3CH_3$ | H | $CH_3$ | N | | |
| 73 | $^tBu$ | $-C\equiv C(CH_2)_3CH_3$ | H | $CH_3$ | CH | 57–59 | |
| 74 | 2,4-diCl—$C_6H_3$ | $-C\equiv CCH_3$ | H | $CH_3$ | N | 168.7–170.8 | |
| 75 | 2,4-diCl—$C_6H_3$ | $-C\equiv CC_2H_5$ | H | $CH_3$ | N | | |
| 76 | 2,4-diCl—$C_6H_3$ | $-CH=CHC_2H_5$ | H | $CH_3$ | N | | cis |
| 77 | 2,4-diCl—$C_6H_3$ | $-CH=CHC_2H_5$ | H | $CH_3$ | N | gum | trans |
| 78 | 2,4-diCl—$C_6H_3$ | $-(CH_2)_3CH_3$ | H | $CH_3$ | N | | |
| 79 | 4-Cl—$C_6H_4$ | $-C\equiv CCH_3$ | H | $CH_3$ | N | | |
| 80 | 4-Cl—$C_6H_4$ | $-C\equiv CC_2H_5$ | H | $CH_3$ | N | | |
| 81 | 4-Cl—$C_6H_4$ | $-C\equiv C(CH_2)_2CH_3$ | H | $CH_3$ | N | | |
| 82 | 4-Cl—$C_6H_4$ | $-CH=CHC_2H_5$ | H | $CH_3$ | N | | cis |
| 83 | 4-Cl—$C_6H_4$ | $-CH=CHC_2H_5$ | H | $CH_3$ | N | | trans |
| 84 | 4-Cl—$C_6H_4$ | $-(CH_2)_3CH_3$ | H | $CH_3$ | N | | |
| 85 | 4-Cl—$C_6H_4$ | $-(CH_2)_4CH_3$ | H | $CH_3$ | N | | |
| 86 | 2,4-diCl—$C_6H_3$ | $-C\equiv C(CH_2)_2CH_3$ | H | $CH_3$ | N | | |
| 87 | 4-F—$C_6H_4$ | $-C\equiv CCH_3$ | H | $CH_3$ | N | | |
| 88 | 4-F—$C_6H_4$ | $-C\equiv CC_2H_5$ | H | $CH_3$ | N | | |
| 89 | 4-F—$C_6H_4$ | $-C\equiv C(CH_2)_2CH_3$ | H | $CH_3$ | N | | |
| 90 | 4-F—$C_6H_4$ | $-CH=CHC_2H_5$ | H | $CH_3$ | N | | cis |
| 91 | 4-F—$C_6H_4$ | $-CH=CHC_2H_5$ | H | $CH_3$ | N | | trans |
| 92 | 4-F—$C_6H_4$ | $-(CH_2)_3CH_3$ | H | $CH_3$ | N | | |
| 93 | 4-F—$C_6H_4$ | $-(CH_2)_4CH_3$ | H | $CH_3$ | N | | |
| 94 | 4-$CF_3$—$C_6H_4$ | $-C\equiv CC_2H_5$ | H | $CH_3$ | N | | |
| 95 | 4-$CF_3$—$C_6H_4$ | $-C\equiv C(CH_2)_2CH_3$ | H | $CH_3$ | N | | |
| 96 | 4-$CF_3$—$C_6H_4$ | $-CH=CHC_2H_5$ | H | $CH_3$ | N | | cis |
| 97 | 4-$CF_3$—$C_6H_4$ | $-CH=CHC_2H_5$ | H | $CH_3$ | N | | trans |
| 98 | 4-$CF_3$—$C_6H_4$ | $-(CH_2)_3CH_3$ | H | $CH_3$ | N | | |
| 99 | 4-$CF_3$—$C_6H_4$ | $-(CH_2)_4CH_3$ | H | $CH_3$ | N | | |
| 100 | 2,4-diCl—$C_6H_3$ | $-C\equiv CC_2H_5$ | H | $C_2H_5$ | N | | |
| 101 | 2,4-diCl—$C_6H_3$ | $-C\equiv C(CH_2)_2CH_3$ | H | $C_2H_5$ | N | | |
| 102 | 4-Cl—$C_6H_4$ | $-C\equiv CC_2H_5$ | H | $C_2H_5$ | N | | |
| 103 | 4-Cl—$C_6H_4$ | $-C\equiv C(CH_2)_2CH_3$ | H | $C_2H_5$ | N | | |
| 104 | $^tBu$ | $-C\equiv C(CH_2)_3CH_3$ | H | $CH_3$ | N | oil | methyl ether |
| 105 | $^tBu$ | $-C\equiv C(CH_2)_2CH_3$ | H | $C_2H_5$ | N | | methyl ether |
| 106 | $^tBu$ | $-CH=CH-C=C-CH_2-CH_3$ | H | $CH_3$ | N | | |
| 107 | $^tBu$ | $-CH_2-CH_2-CH=CH-CH_2-CH_3$ | H | $CH_3$ | N | | |
| 108 | $^tBu$ | $-C\equiv C-CH_2-CH=CH-CH_2-CH_3$ | H | $CH_3$ | N | | |
| 109 | $^tBu$ | $CH=CHCH_2CH(CH_3)_2$ | H | $CH_3$ | N | 64–66 | trans |
| 110 | $^tBu$ | $CH=CHCH(CH_3)_2$ | $CH_3$ | $CH_3$ | N | oil | trans |

TABLE I-continued

| NO. | $R_1$ | $R_2$ | $R_3$ | $R_4$ | Y | M.pt. (°C.) | COMMENTS |
|---|---|---|---|---|---|---|---|
| 111 | $^tBu$ | $CH=CHCH_2CH(CH_3)_2$ | H | $C_2H_5$ | N | 60–64 | trans |
| 112 | $^tBu$ | $CH=CHCH(CH_3)C_2H_5$ | H | $C_2H_5$ | N | 64–67 | trans |
| 113 | $^tBu$ | $CH=CH^tBu$ | H | $C_2H_5$ | N | 78–82 | trans |
| 114 | $^tBu$ | $CH=CHCH_2CH(CH_3)_2$ | H | $C_2H_5$ | N | 66–69 | cis |
| 115 | $^tBu$ | $CH=CHCH(CH_3)C_2H_5$ | H | $C_2H_5$ | N | 60–62.5 | cis |
| 116 | $^tBu$ | $CH=CH^tBu$ | H | $C_2H_5$ | N | 94–98 | mixture of cis and trans |
| 117 | $^tBu$ | $CCl=Cl(CH_2)_2CH_3$ | H | $CH_3$ | N | 95–98.5 | mixture of cis and trans |
| 118 | $^tBu$ | $CCl=CCl(CH_2)_3CH_3$ | H | $CH_3$ | N | 90–92.5 | mixture of cis and trans |
| 119 | $^tBu$ | $C≡C(CH_2)_2CH_3$ | H | $(CH_2)_2CH_3$ | N | 103–105 | |
| 120 | $^tBu$ | $C≡CCH(CH_3)_2$ | H | $(CH_2)_2CH_3$ | N | 93–95 | |
| 121 | $^tBu$ | $C≡C(CH_2)_2CH_3$ | —$CH_2CH_2$— | | N | oil | |
| 122 | $^tBu$ | $(CH_2)_3CH_3$ | $CH_3$ | $CH_3$ | N | oil | |
| 123 | $^tBu$ | $(CH_2)_2CH(CH_3)_2$ | $CH_3$ | $CH_3$ | N | | |
| 124 | $^tBu$ | $(CH_2)_3CH(CH_3)_2$ | H | $C_2H_5$ | N | 65–68.5 | |
| 125 | $^tBu$ | $(CH_2)_2CH(CH_3)C_2H_5$ | H | $C_2H_5$ | N | | |
| 126 | $^tBu$ | $(CH_2)_2CH(CH_3)_2$ | H | $CH_3$ | N | | |
| 127 | $^tBu$ | $(CH_2)_4CH(CH_3)_2$ | H | $CH_3$ | N | | |
| 128 | $^tBu$ | $(CH_2)_2$-cyclopentyl | H | $CH_3$ | N | gum | |
| 129 | $^tBu$ | $CH_2$-cyclohexyl | $CH_3$ | $CH_3$ | N | | |
| 130 | $^tBu$ | $CH=CH^tBu$ | H | $C_2H_5$ | N | | mixture of cis and trans |
| 131 | $^tBu$ | $CH_2C≡C(CH_2)_2CH_3$ | H | $CH_3$ | N | 47–51 | isomer A |
| 132 | $^tBu$ | $CH_2C≡C(CH_2)_2CH_3$ | H | $CH_3$ | N | 83–86 | isomer B |
| 133 | $^tBu$ | $CH_2C≡CCH_3$ | H | $CH_3$ | N | 105.5–105.6 | |
| 134 | $^tBu$ | $CH_2C≡CH(CH_3)C_2H_5$ | H | $CH_3$ | N | oil | 32:68 mixture of isomers |
| 135 | $^tBu$ | $CH_2C≡CCH(CH_3)_2$ | H | $CH_3$ | N | oil | 32:68 mixture of isomers |
| 136 | $^tBu$ | $CH_2C≡CCH_2CH(CH_3)_2$ | H | $CH_3$ | N | oil | 31:69 mixtures of isomers |
| 137 | $^tBu$ | $C≡C(CH_2)_2CH_3$ | H | F | N | 73–77 | isomer A |
| 138 | $^tBu$ | $C≡C(CH_2)_2CH_3$ | H | F | N | oil | isomer B |
| 139 | $^tBu$ | $C≡CCH_2CH(CH_3)_2$ | H | $OCH_3$ | N | 121.7–122.7 | |
| 140 | $^tBu$ | $C≡C^tBu$ | H | $C_2H_5$ | N | 122–124.5 | |
| 141 | $^tBu$ | $C≡C^tBu$ | H | $CH_3$ | N | 104–106.5 | isomer A |
| 142 | $^tBu$ | $C≡C^tBu$ | H | $CH_3$ | N | 108.5–110.2 | isomer B |
| 143 | $^tBu$ | $C≡CSi(CH_3)_3$ | H | $CH_3$ | N | 104.5–107 | isomer A |
| 144 | $^tBu$ | $C≡CSi(CH_3)_3$ | H | $CH_3$ | N | 91–94 | isomer B |
| 145 | $^tBu$ | $C≡CCH_2$-cyclopropyl | H | $CH_3$ | N | 111–114.5 | |
| 146 | $^tBu$ | $C≡C(CH_2)_3Cl$ | H | $CH_3$ | N | 89–93 | |
| 147 | $^tBu$ | $C≡CH$ | H | $CH_3$ | N | 127 ∝ 129 | |
| 148 | $^tBu$ | $C≡CH$ | H | $CH_3$ | N | | |
| 149 | $^tBu$ | $C≡CCH_2OH$ | H | $CH_3$ | N | 144–146 | |
| 150 | $^tBu$ | $C≡CCH_2OCH_3$ | H | $CH_3$ | N | 136–137 | isomer A |
| 151 | $^tBu$ | $C≡CCH_2OCH_3$ | H | $CH_3$ | N | oil | 87:13 mixture of isomers |
| 152 | $^tBu$ | $C≡CCH_2O(CH_2)_3CH_3$ | H | $CH_3$ | N | 99.8–100.4 | isomer A |
| 153 | $^tBu$ | $C≡CCH_2O(CH_2)_3CH_3$ | H | $CH_3$ | N | 55.1–57.8 | isomer B |
| 154 | $^tBu$ | $C≡CC(CH_3)_2OCH_3$ | H | $CH_3$ | N | 105–106 | |
| 155 | $^tBu$ | $CH=CHC(CH_3)_2OCH_3$ | H | $CH_3$ | N | 100–102 | |
| 156 | $^tBu$ | $C≡CCH(OC_2H_5)_2$ | H | $CH_3$ | N | 109–110 | |
| 157 | $^tBu$ | $C≡CCO_2C_2H_5$ | H | $CH_3$ | N | 125–7 | 96:4 mixture of isomers |
| 158 | $^tBu$ | $C≡CCH=NOH$ | H | $CH_3$ | N | 114–116 | mixture of cis and trans |
| 159 | $^tBu$ | $C≡CCH=NOCH_2Ph$ | H | $CH_3$ | N | 115–117 | mixture of cis and trans |
| 160 | $^tBu$ | —$(CH_2)_2$—$CH(CH_3)$—$C_2H_5$ | H | $C_2H_5$ | N | 50–53.5 | |
| 161 | $^tBu$ | —$(CH_2)_4$—$CH(CH_3)_2$ | H | $CH_3$ | N | gum | 3:1 mixture of isomers |
| 162 | $^tBu$ | —$(CH_3)_4$—$CH_3$ | H | $CH_3$ | N | oil | isomer A |
| 163 | $^tBu$ | —$(CH_2)_4$—$CH_3$ | H | $CH_3$ | N | oil | isomer B |
| 164 | $^tBu$ | —$(CH_2)_2$—$CH(CH_3)_2$ | H | $CH_3$ | N | oil | isomer A |
| 165 | $^tBu$ | —$(CH_2)_4$—$CH_3$ | $CH_3$ | $CH_3$ | N | oil | |

TABLE I-continued

| NO. | $R_1$ | $R_2$ | $R_3$ | $R_4$ | Y | M.pt. (°C.) | COMMENTS |
|---|---|---|---|---|---|---|---|
| 166 | $^tBu$ | $-(CH_2)_2-CH(CH_2)_2$ | $CH_3$ | $CH_3$ | N | oil | |
| 167 | $^tBu$ | $-C\equiv CCH_2-$ | H | $CH_3$ | N | 68-72 | isomer A |
| 168 | $^tBu$ | $-C\equiv CCH_2-$ | H | $CH_3$ | N | 111-113 | isomer B |
| 169 | $^tBu$ | $-(CH_2)_3-CH(CH_3)_2$ | H | $OCH_3$ | N | 54-55.5 | |
| 170 | $^tBu$ | $-(CH_2)_3CH(CH_3)C_2H_5$ | H | $CH_3$ | N | oil | 45:55 mixture of isomer |
| 171 | $^tBu$ | $-(CH_2)_3CH_3$ | H | $CH_3$ | N | oil | 72:28 mixture of isomer |
| 172 | $^tBu$ | $-(CH_2)_3-O(CH_2)_3CH_3$ | H | $CH_3$ | N | oil | |

Key:

$^tBu$ = tertiary butyl i.e. $-\underset{\underset{CH_3}{|}}{\overset{\overset{CH_3}{|}}{C}}-CH_3$ Certain of the compounds listed in Table I which were gum or oils, for which the melting point could be obtained, were further characterised as follows:

Compound No. 46

NMR (CDCl$_3$): 0.56 (3H, t); 0.72 (9H, s); 0.77-1.04 (3H, complex); 1.1-1.5 (4H, complex); 1.9-2.3 (2H, complex); 2.3-2.64 (2H, complex); 3.72 (1H, s); 4.1-4.4 (1H, complex); 5.1-5.7 (2H, complex); 8.01 (1H, s); 8.20 (1H, s).

IR (film): 3650-3150, 3120, 1658.

m/e: no M$^+$, 264, 222, 169, 153, 111, 82.

Analysis: $C_{16}H_{29}N_3O$ requires: C, 68.77; H, 10.46; N, 15.04%. found: C, 68.34; H, 10.47; N, 14.99%.

Compound No. 47

NMR (CDCl$_3$): 0.55 (3H, t); 0.70 (9H, s); 0.95 (3H, t); 1.25-1.45 (4H, complex); 1.85-2.05 (2H, complex); 2.06-2.20 (2H, complex); 3.83 (1H, s); 4.33-4.40 (1H, complex); 5.45-5.55 (1H, complex); 5.75-5.86 (1H, complex); 7.95 (1H, s); 8.25 (1H, complex).

IR (film): 3650-3100, 3130 cm$^{-1}$.

m/e: no. M$^+$, 264, 222, 169, 111, 82.

Analysis: $C_{16}H_{29}N_3O$ requires: C, 68.77; H, 10.46: N, 15.04%. found: C, 68.07; H, 10.84; N, 14.83%.

Compound No. 51a

IR: 3375 cm$^{-1}$, 3110 cm$^{-1}$.

NMR (δ) 0.88 (12H, m); 1.28 (8H, m); 1.56 (3H, d); 1.7 (2H, m); 3.4 (1H, s); 4.72 (1H, q); 7.92 (1H, s); 8.2 (1H, s).

Compound No. 51b

IR: 3350 cm$^{-1}$, 3110 cm$^{-1}$.

NMR (δ) 0.86 (3H, m); 0.96 (9H, s); 1.2 (10H, m); 1.64 (3H, d); 3.88 (1H, s); 4.74 (1H, q); 7.88 (1H, s); 8.32 (1H, s).

Compound No. 67

IR $\nu$OH 2500-1900 cm$^{-1}$ (broad).

NMR (CDCl$_3$): 0.8-1.8(m, 11H); 0.9 9H); 1.63 (d) 2.87 (s); 4.60 (q); 7.93 (s) 1H; 9.16 (s) 1H.

Mass spec EI: No. M$^+$ observable.

m/e: 208, 182, 97, 82, 70.

Compound No. 121

NMR (CDCl$_3$): 0.84 (9H, s); 1.00 (3H, t); 1.2-1.84 (6H, complex); 2.22 (2H, complex) ; 3.79 (1H, s); 7.85 (1H, s); 8.46 (1H, s).

IR (film): 3700-3050, 2240.

m/e: No. M$^+$, 246, 204, 108, 70.

Analysis: $C_{15}H_{23}N_3O$, requires: C, 68.93; H, 8.87; N, 16.08%. found: C, 68.25; H, 8.67; N, 16.26%.

Compound No. 122

NMR (CDCl$_3$): 0.84 (3H, tJ8 Hz); 0.86 (9H, s); 0.9-1.8 (6H, complex); 1.68 (3H, s); 1.81 (3H, s); 4.20 (1H, broad, s); 7.94 (1H, s); 8.20 (1H, s).

IR (film) 2800-3600 cm$^{-1}$.

m/e: No. M$^+$, 238, 196, 111, 96.

Analysis: $C_{14}H_{27}N_3O$ requires: C, 66.36; H, 10.74; N, 16.58. found: C, 66.24; H, 10.19; N, 16.73.

Compound No. 128

NMR (CDCl$_3$) δ ppm: 0.8-1.8 (m, 13H); 0.97 (s, 9H); 1.66 (d, 3H); 3.19 (s, 1H); 4.69 (q, 1H); 7.94 (s, 1H); 8.17 (s, 1H).

GC 100%.

MS CI, ammonia MH$^+$ 280. EI, 280 (1%), 222 (12%), 183 (20%), 182 (33%), 97 (74%) 57 (84%), 41 (100%).

CHN Expected: C, 68.78; H, 10.46; N, 15.04. Found: C, 69.49; H, 10.71; N, 14.69.

Compound No. 163

NMR (CDCl$_3$): 0.86 (9H, s); 0.70-1.00 (3H, complex); 1.04-1.45 (6H, complex); 1.57 (3H, d); 1.46-1.85 (2H, complex); 3.46 (1H, s); 4.73 (1H, quartet); 7.93 (1H, s); 8.21 (1H, s).

IR (film): 3650-3050, 3125.

m/e: MH$^+$ 254 due to self CI. 236, 196, 182, 157, 97, 82.

Analysis: $C_{14}H_{27}N_3O$ requires: C, 66.36; H, 10.74; N, 16.58%. found: C, 65.89; H, 11.06; N, 16.75%.

Compound No. 164

NMR (CDCl$_3$): 0.82 (6H, d); 1.01 (9H, s). 1.00–1.85 (5H, complex); 1.68 (3H, d); 3.39 (1H, s); 4.71 (1H, quartet); 7.93 (1H, s); 8.20 (1H, s).

IR (film): 3650–3050, 3125.

m/e: No. M+, 196, 182, 157, 97, 82.

analysis: C$_{14}$H$_{27}$N$_3$O requires: C, 66.36; H, 10.74; N, 16.58%. found: C, 66.28; H, 10.40; N, 16.64%.

Compound No. 166

NMR (CDCl$_3$):0.50–0.78 (6H, complex); 0.70 (9H, s); 0.80–1.80 (5H, complex); 1.50 (3H, s); 1.64 (3H, s); 4.12 (1H, s); 7.75 (1H, s); 8.06 (1H, s).

IR (film): 3650–3150, 3125.

m/e: No. M+, 210, 196, 157, 141, 123, 111, 96, 83.

analysis: C$_{15}$H$_{29}$N$_3$O requires: C, 67.37; H, 10.93; N, 15.71%. found: C, 67.31; H, 10.63; N, 15.57%.

Examples of salts of compound No. 1 of Table I are shown in Table II below in which the acid from which the salt is derived by reaction with the hydroxy group is indicated in column 1.

TABLE II

| Acid | Melting point of salt with compound No. 1 (°C.) |
|---|---|
| HBr | 92–96 |
| HCl | 130–135 |
| 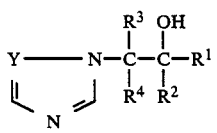 CH$_3$—⟨⟩—SO$_3$H | gum |
| C$_{12}$H$_{25}$—⟨⟩—SO$_3$H | oil |

The compounds of general formula (I):

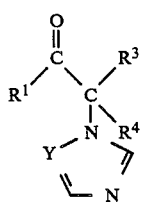

$$Y-N-\underset{R^4}{\overset{R^3}{C}}-\underset{R^2}{\overset{OH}{C}}-R^1 \quad \text{(I)}$$

may be prepared by reacting a compound of general formula (IIa) or (IIb):

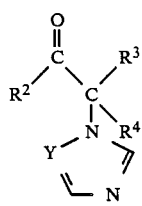

(IIa)

(IIb)

wherein R$^1$, R$^2$, R$^3$, R$^4$ and Y are as defined above, with an organometallic compound of general formula (IIIb) or (IIIa) respectively:

$$R^1M \quad \text{(IIIa)}$$

$$R^2M \quad \text{(IIIb)}$$

wherein R$^1$ and R$^2$ are as defined above and M is a metal which is preferably lithium, magnesium, titanium, copper, aluminium or zirconium (when M is magnesium or zirconium the organometallic compound is more specifically R$^1$ Mg halogen or R$^2$ Mg halogen. When M is titanium the organometallic compound is more specifically R$^1$Ti(O-alkyl)$_3$ or R$^2$Ti(O-alkyl)$_3$. When M is zirconium the organometallic compound is more specifically R$^1$Zr(O-alkyl)$_3$ or R$^2$Zr(O-alkyl)$_3$). The reaction conveniently takes place in solvent such as diethyl ether, tetrahydrofuran or dichloromethane at −80° C. to +80° C. in an inert atmosphere. The product is worked up by quenching with a proton donor.

The compounds of general formula (I) may also be prepared by reacting a compound of general formula (IV) or (V):

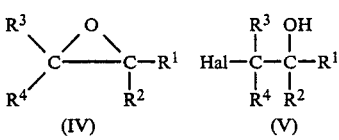

(IV)      (V)

in which R$^1$, R$^2$, R$^3$ and R$^4$ are as defined above and Hal is a halogen atom (preferably a chlorine or bromine atom), with 1,2,4-triazole or imidazole either in the presence of an acid-binding agent or in the form of one of its alkali metal salts in a convenient solvent.

Suitably the compound of general formula (IV) or (V) is reacted at 20°–100° C. with sodium salt of 1,2,4-triazole or imidazole (the salt can typically be prepared by adding either sodium hydride or sodium methoxide to 1,2,4-triazole or imidazole) in a convenient solvent such as acetonitrile, methanol, ethanol or dimethylformamide. The product can be isolated by pouring the reaction mixture into water and extracting the product with a suitable organic solvent eg. diethyl ether, ethyl acetate or dichloromethane.

The ethers and the esters of the invention are made from the hydroxy compounds by reacting them with the appropriate halide, sulphonate, acid chloride, acid anhydride or sulphonyl chloride in the presence of a suitable base.

The compounds of general formula (V) can be prepared by reacting the appropriate compound of general formula (VI):

(VI)

wherein R$^1$ and R$^2$ are defined as above with sulphonium ylides such as (VII) (see JACS 1973 95 1285):

(VII)

The ketones of general formula (VI) may be prepared using standard methods set out in the literature.

Compounds of the general formula (IV) and (V) may also be prepared by reacting a compound of general formula (VIIIa) or (VIIIb):

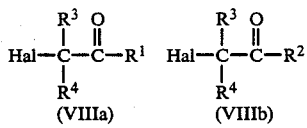

wherein $R^1$, $R^2$, $R^4$ and Hal are as defined above, with an organometallic compound of general formula (IIIa) or (111b) above.

The compounds of general formula (VIII) may be made by standard methods set out in the literature.

Compounds of the general formula (IIa) may be prepared by reacting a compound of general formula (IXa) or (IXb):

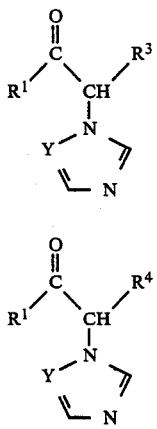

wherein $R^1$, $R^3$, $R^4$ and Y are as defined above, with the compounds of the general formula (Xa) or (Xb):

$R^3Hal$      (Xa)

$R^4Hal$      (Xb)

wherein $R^3$, $R^4$ and Hal are as described above, in a convenient solvent such as methanol, ethanol, tetrahydrofuran or dimethylformamide in the presence of a suitable base.

Compounds of the general formula (IIb) may be prepared by reacting a compound of general formula (XIa) or (XIb):

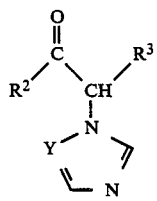

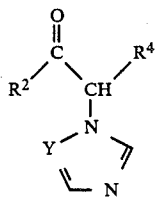

wherein $R^2$, $R^3$, $R^4$ and Y are as defined above with compounds of the general formula (Xa) or (Xb), in a suitable solvent such as methanol, ethanol, tetrahydrofuran or dimethylformamide in the presence of a suitable base such as sodium hydride.

Compounds of the general formula (IIa) and (IIb) may be prepared by reacting a compound of general formula (VIIIa) or (VIIIb) with 1,2,4-triazole or imidazole either in the presence of an acid binding agent or in the form of one of its alkali metal salts in a convenient solvent such as acetonitrile, methanol, ethanol or dimethylformamide.

Compounds of the general formula (IV), (IX), (XI) may be prepared by methods set out in the literature.

The olefinic azolyl alcohols (XII), where $R^2$ is $CH=CHX$, $R^1$, $R^3$, $R^4$ and Y are as defined above and $n=0$ can also be made by reduction of the acetylenic azolylalcohols (XIII) using either hydrogen in the presence of a suitable catalyst such as palladium on carbon (or other supports) or a metal hydride reagent such as lithium aluminium hydride, Red-Al (sodium bis (2-methoxyethoxy)aluminium hydride) or sodium borohydride/palladium (II) chloride in a suitable solvent such as ether or tetrahydrofuran.

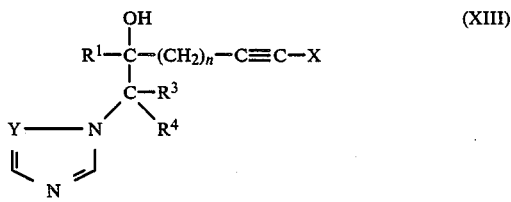

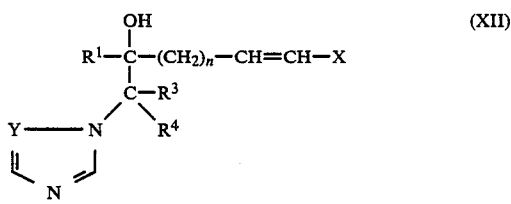

The alkyl azolyl alcohols (XIV), where $R^2$ is $CH_2CH_2X$, $R^1$, $R^3$, $R^4$, Y and m are as defined above can also be made by the reduction of the olefinic alcohols (XII) or by the reduction of the acetylenic alcohols (XIII) using hydrogen in the presence of a suitable catalyst such as palladium on carbon (or other supports) in a suitable solvent such as methanol, ethanol or acetic acid.

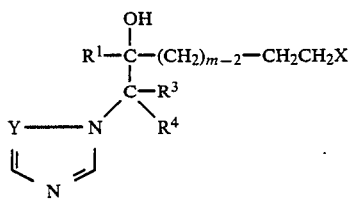

(XIV)

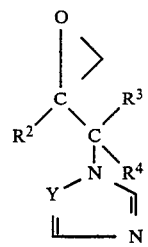

(XVb)

A compound of general formula (XIII) wherein R$^1$, R$^3$, R$^4$, X, Y and n are defined as above may be prepared by treatment of the di-metal salt of a compound of the general formula (XIII) wherein R$^1$, R$^3$, R$^4$, Y and n are defined as above but with hydrogen in place of the group X with an appropriate derivative of the group X, for example a halide or sulphonate.

Suitably the compound of general formula (XIII) having hydrogen in place of the group X is reacted at −80° C. to +80° C. with at least two equivalents of a suitable base such as lithium amide in a convenient solvent such as liquid ammonia, or tetrahydrofuran to form the dimetal salt. The dimetal salt is then reacted with a suitable halide (ie. XCl) at −80° C. to +80° C. The product can be isolated by pouring the reaction mixture into water and extracting the product with a suitable organic solvent.

Compounds of general formula (XIII) and (XII) may be treated with reagents known to add to carbon-carbon multiple bonds. Suitably a compound of general formula (XII) or (XIII) is reacted between −80° C. and +80° C. with such a reagent, for example a halogen such as chlorine or the complex formed between lithium chloride and copper (II) chloride in a convenient solvent such as dichloromethane, chloroform, acetonitrile or tetrahydrofuran.

Compounds of the general formula (XII), (XIII) or (XIV) wherein X contains suitable functional groups such as an acetal, a ketone, an hydroxyl, an halide or an ester may be further transformed using methods set out in the literature. For example an acetal may be further transformed by treatment with an hydroxylamine salt between 0° and +120° C. in a convenient solvent such as ethanol, methanol or water.

Thus for example Compound No. 159 in Table I may be prepared by treatment of compound No. 156 with aqueous 0-benzyl hydroxylamine hydrochloride under reflux. Compounds of general formula I may be prepared by reacting a compound of general formula (XVa) or (XVb) wherein R$^1$, R$^2$, R$^3$ are as defined previously

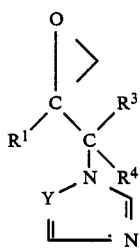

(XVa)

with an organometallic reagent (IIIb) or (IIIa) respectively in a convenient solvent such as diethyl ether or tetrahydrofuran at −80° C. to +80° C. in an inert atmosphere. The product is worked up by quenching with a proton donor.

Compounds of general formula (XVa) and (XVb) may be prepared by reacting a compound of general formula (IIa) or (IIb) with dimethylsulphonium methylide (JACS 1962, 84, 3782) or dimethylsulphoxonium methylide (JACS 1965, 87, 1353) using methods set out in the literature.

The compounds, and their derivatives as defined above, also have plant growth regulating activities.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata, Festuca* spp. (eg. *Festuca rubra*) and *Poa* spp. (eg. *Poa pratense*). The compounds may stunt grasses without significant phytotoxic effects and without deleteriously affecting the appearance (particularly the colour) of the grass; this makes such compounds attractive for use on ornamental lawns and on grass verges. They may also haven an effect on flower head emergence in, for example, grasses. The compounds can also stunt weed species present in the grasses; examples of such weed species are sedges (eg. Cyperus spp.) and dicotyledonous weeds (eg. daisy, plantain, knotweed, speedwell, thistle, docks and ragwort). The growth of non-crop vegetation (eg. weeds or cover vegetation) can be retarded thus assisting in the maintenance of plantation and field crops. In fruit orchards, particularly orchards subject to soil erosion, the presence of grass cover is important.

However excessive grass growth requires substantial maintenance. The compounds of the invention could be useful in this situation as they could restrict growth without killing the plantts which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturising ornamental, household, garden and nursery plants (eg. poinsettias, chrysanthemums, carnations, tulips and daffodils).

As indicated above, the compounds can also be used to stunt woody species. This property can be used to control hedgerows or to shape or reduce the need for pruning, of fruit trees (eg. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, eg. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (eg. rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such as way as to increase yield. In the treatment of rice plants, or rice crops the invention compounds can be applied, eg. as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, eg. improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (eg. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (ie. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus provides a fungicidal or plant growth regulating composition comprising a compound of general formula (I) as hereinbefore defined, or a salt or metal complex thereof; and, optionally, a carrier or diluent.

The invention also provides a method of combating fungi, which comprises applying to a plant, to seed of a plant, or to the locus of the plant or seed, a compound, or salt or metal complex thereof as hereinbefore defined; or a composition containing the same.

The invention also provides a method of regulating plant growth, which comprises applying to the plant, to seed of a plant or to the locus of a plant or seed, a compound, or a salt or metal complex thereof, as hereinbefore defined, or a composition combining the same.

In the foregoing process compound No 1 of Table I is especially useful.

The compounds, salts, metal complexes, ethers and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatement. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (eg. 2-ethoxyethanol and 2-butoxyethanol).

The compositions to be used as sprays may also be in the form of aerosols wherein the formulation is held in a container under pressure in the presence of a propellant, eg. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adpated for various utilities.

The compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants eg. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (eg. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also other compound(s) having biological activity, eg. compounds having similar or complementary fungicidal or plant growth activity or compounds having plant growth regulating, herbicidal or insecticidal activity.

The other fungicidal compound can be, for example, one which is capable of combating ear diseases of cereals (eg. wheat) such as Septoria, Gibberella and helminthosporium spp., seed and soil borne diseases and downy and powdery mildews on grapes and powdery mildew and scab on apple etc. These mixtures of fungicides can have a broader spectrum of activity than the compound of general formula (I) alone; further theother fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetyl-aluminium, carboxin, nitrotal-isopropyl, triadimefon, thiabendazole, etridiazole, triadimenol, biloxazol, dithianon, binapacryl, quinomethionate, guazatine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenaponil, ofurace, propiconazole, etaconazole and fenpropemorph and fenpropidine.

The compounds of general formula (I) can be mixed with soil, peat or other rooting media for the protection of plants against seed-borne, soil-borne or foliar fungal diseases.

Suitable insecticides are Pirimor, Croneton, dimethoate, Metasystox and formothion.

The other plant growth regulating compound can be one which controls weeds or seedhead formation, improves the level or longevity of the plant growth regulating activity of the compounds of general formula (I), selectively controls the growth of the less desirable plants (eg. grasses) or causes the compound of general formula (I) to act faster or slower as a plant growth regulating agent. Some of these other agents will be herbicides.

Examples of suitable plant growth regulating compounds, which can display esynergy in admixture, or use, with the invention compounds are the gibberellins (eg. GA3, GA4 or GA7), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acids 8eg. triiodobenzoic acid), morphactins (eg. chlorfluorecol), maleic hydrazide, glyphosate, glyophosine, long chain fatty alcohols and acids, dikegulac, fluoridamid, mefluidide, substituted quaternary ammonium and phosphonium compounds (eg. chlormequat* chlorphonium or mepiquat chloride*), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat*, benzoylpropethyl 3,6-dichloropicolinic acid, fenpentezol, triapenthanol, flurpirimidol, paclobutrazol, tetrcyclacis and tecnazene. Synergy will be most likely to occur with those of the foregoing which are quaternary ammonium compounds and with those marked with an asterisk.

The use of the compounds of general formula (I) in conjunction with gibberellins can be useful where it is desired to reduce the plant growth regulating effects of the compounds (eg. where they are to be used as fungicides). Where the compounds are being applied to the soil surrounding the plants or to the roots of the plant, the plant growth regulating effects of the compounds may possibly be reduced by using also certain types of phenoxybenzoic acids and their derivatives.

The following Examples illustrate the invention; the temperatures are given in degrees Centigrade (°C.). The abbreviation 'THF' stands for the solvent tetrahydrofuran.

EXAMPLE 1

This Example illustrates the preparation of the compound having the structure:

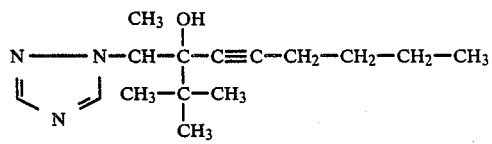

To a solution of hex-1-yne (1.80 g, 0.022M) in dry tetrahydrofuran (20 mls) at 0° C., under nitrogen, was added dropwise n-butyl lithium (14 mls of a 1.5M solution in hexane). When the addition was complete the resulting clear yellow solution was left to stir for a further 15 minutes at 0° C. To this solution was added dropwise a solution of 2,2-dimethyl-4-(1,2,4-triazol-1-yl)-pentan-3-one (2.92 g, 0.016M) in dry tetrahydrofuran (20 mls). The resulting mixture was left to stir at room temperature for 16 hrs, ethanol (5 mls) was then added to the mixture and the solvent removed in vacuo. The residue was partitioned between water and ethyl acetate. The aqueous portion was further extracted with ethyl acetate (2x). The combined ethyl acetate extracts were washed with brine, dried (anhydrous MgSO4) and then concentrated in vacuo to give a cream solid. Chromatography on silica using gradient elution (diethyl ether (0–60%) in petrol) gave the pure triazolyl alcohol as a cream solid. Trituration with petrol (40–60) removed the colour leaving the product (1.82 g) (m.pt. 90°–92° C.) as a white solid.

NMR (CDCl3) 0.90 (3H, t, J 7 Hz), 0.91 (9H, s), 1.2–1.6 (4H, cmplx), 1.74 (3H, d J 8 Hz), 2.24 (2, H, cmplx), 3.37 (1H, s), 4.74 (1H, q, J 8 Hz), 7.91 (1H, s), 8.24 (1H, s).

IR (nujol) 2500–3500 (strong), 2230 (weak) cm$^{-1}$.

m/e: no. M+, 248, 206, 97, 82.

EXAMPLE 2

This Example illustrates the separation of compound No 1 of Table I into separate isomers A and B.

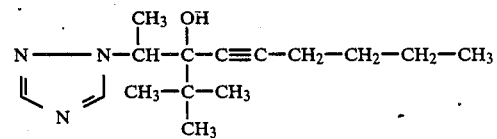

Isomer A — Compound No 1 of Table I

Isomer B — Compound No 2 of Table I

To a solution of hex-1-yne (19.03 g, 0.232M) in dry tetrahydrofuran (200 mls) at −25° C., under Argon, was added dropwise n-butyl lithium (147.2 mls) of a 1.55M solution in hexane, 0.228M). The resulting solution was stirred at −10° C. for 10 mins then cooled to −50° C. To this solution was added dropwise a solution of 2,2-dimethyl-4-(1,2,4-triazol-1-yl)-pentan-3-one (35.0 g, 0.193M) in dry tetrahydrofuran (150 mls). The resulting solution was stirred at −60° C. for 10 mins and then allowed to warm to 0° d C. over ¾ hr. Methanol (10 ml) was then added, followed by water (400 mls) and brine (200 mls). The organic layer was separated and the aqueous portion further extracted with diethyl ether. The combined organic extracts were washed with water, dried (anhydrous MgSO4) and then concentraed in vacuo to give a pale yellow oil which gradually crystalized. Trituration with petrol (30–40) containing a trace of diethyl ether then filtration gave isomer A (43.27 g) (m.pt. 90°-2° C.) as a white crystalline solid. The filtrates were chromatographed on silica (Merck Art 7729) using dichloromethane:diethyl ether (5:1) as eluent. This gave isomer B (1.556 g) (b.pt. 150°-180° C./0.2 mm Mercury) $n^{25}D$ 1.4918) as a pale yellow viscous oil.

Isomer A

NMR (CDCl3) 0.89 (12H, complx), 1.2–1.6 (4H, complx), 1.73 (3H, d J 8 Hz), 2.24 (2H, t J 7 Hz), 4.12 (1H, s), 4.78 (1H, q J 8 Hz), 7.87 (1H, s), 8.27 (1H, s).

IR (nujol) 3170 (medium, broad), 2230 (very weak) cm$^{-1}$.

m/e: no. M+, 248, 206, 97, 82.

Analysis: $C_{15}H_{25}N_3O$ requires: C, 68.40; H, 9.57; N, 15.95%. found: C, 68.40; H, 9.48; N, 16.19%.

Isomer B

NMR (CDCl3) 0.95 (12H, cmplx), 1.2–1.6 (4H, cmplx), 1.66 (3H, d J 3 Hz), 2.19 (2H, t J 3 Hz), 3.49 (1H, s), 4.75 (1H, q J 3 Hz), 7.89 (1H, s), 8.34 (1H, s).

IR (film) 3100–3500 (medium, broad), 2240 (weak) cm$^{-1}$.

m/e: no. M+, 248, 206, 167, 97, 82.

EXAMPLE 3

This Example illustrates the preparation of the compound having the structure:

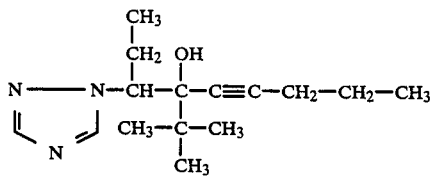

(Compound No 8 of Table I)

To a solution of pent-1-yne (2.45 g, 0.036M) in dry tetrahydrofuran (30 mls) at 0° C., under nitrogen was added dropwise n-butyl lithium (22.6 mls of a 1.55M solution in hexane). When the addition was complete the resulting solution was stirred at 0° C. for 15 minutes then cooled to −78° C. To this solution was added dropwise a solution of 2,2-dimethyl-4-(1,2,4-triazol-1-yl)-hexan-3-one (5.01 g, 0.0257M) in dry tetrahydrofuran (50 mls). The mixture was then allowed to warm to room temperature over 1 hour and then quenched by the addition of methanol (2 mls). The solvent was removed in vacuo and the residue partitioned between water and diethyl ether. The aqueous portion was further extracted with ether (2×). The Combined etherial extracts were washed with brine, dried (anhydrous MgSO4) and then concentrated in vacuo to give a pale yellow solid. Trituration with petrol (40–60) gave the product as a 98:2 mixture of isomers (6.39 g) (m.pt. 99°-101° C.).

NMR (CDCl3) 0.62 (3H, t J 8 Hz), 0.82 (9H, s), 1.0 (3H, t, J 8 Hz), 1.56 (2H, sextet, J 8 Hz), 1.9–2.6 (2H, cmplx), 2.23 (2H, t, J 8 Hz), 3.42 (1H, s), 4.42 (1H, dd J 8, 4 Hz), 7.94 (1H, s), 8.20 (1H, s).

IR (nujol) 2500–3500 (strong), 2220 (weak) cm$^{-1}$.

m/e: no. M+, 248, 206, 153, 138, 111, 96, 82.

EXAMPLE 4

This Example illustrates the preparation of compounds Nos 3 and 4 of Table I, as Isomers A and B of the compound having the structure:

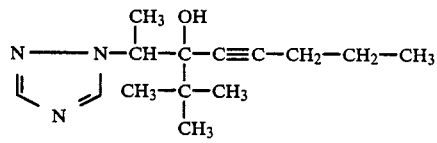

Isomer A — Compound No 3 of Table I

Isomer B — Compound No 4 of Table I

To a solution of pent-1-yne (1.36 g, 0.020M) in dry tetrahydrofuran (20 mls) at 0° C., under nitrogen was added dropwise ethyl magnesium bromide (6.3 mls of a 3M solution in diethyl ether). The resulting mixture was then heated at reflux for 1 hr and then cooled to 0° C. To this mixture was added dropwise a solution of 2,2-dimethyl-4-(1,2,4-triazol-1-yl)-pentan-3-one (2.72 g, 0.015M) in dry tetrahydrofuran (20 mls). The resulting mixture was left to stir at room temperature for 16 hrs, ethanol (5 mls) was then added and the solvent removed in vacuo. The residue was partitioned between water and ethyl acetate. The aqueous portion was further extracted with ethyl acetate (2×). The combined ethyl acetate extracts were washed with brine, dried (anhydrous MgSO4) and then concentrated in vacuo to give a pale yellow oil. Chromatography on silica using gradient elution (diethyl ether (0–50%) in petrol) gave isomer A (1.0 g) (m.pt. 76°-78° C.) as a white solid and isomer B (0.26 g) (m.pt. 110°-112° C.) as a white solid.

Isomer A

NMR (CDCl3) 0.97 (12H, cmplx), 1.2–1.6 (2H cmplx), 1.68 (3H, d J 8 Hz), 2.15 (2H, t J 7 Hz), 2.87 (1H, broad s), 4.70 (1H, q J 8 Hz), 7.89 (1H, s), 8.30 (1H, s).

IR (nujol) 2500–3500 (strong), 2230 (weak) cm$^{-1}$.

m/e: no. M+, 234, 192, 97, 82.

Analysis: $C_{14}H_{23}N_3O$ requires: C, 67.46; H, 9.24; N, 16.87%. found: C, 67.46; H, 9.72; N, 16.89%.

Isomer B

NMR (CDCl3) 0.91 (9H, s), 0.97 (3H, t J 7 Hz), 1.2–1.6 (2H. cmplx), 1.74 (3H, d J 8 Hz), 2.22 (2H, t J 7 Hz), 3.31 (1H, s), 4.75 (1H, q J 8 Hz), 7.92 (1H, s) 8.23 (2H, s).

IR (nujol) 2500–3500 (strong) cm$^{-1}$.

m/e: no. M+, 234, 192, 153, 97, 82, 70.

Analysis: $C_{14}H_{23}N_3O$ requires: C, 67.46; H, 9.24; N, 16.87%. found: C, 67.42; H, 8.94; N, 16.83%.

EXAMPLE 5

This Example illustrates the preparation of the compound having the structure:

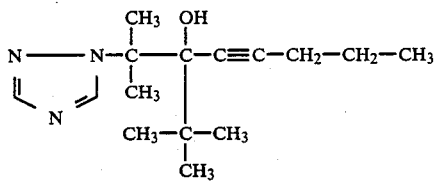

(Compound No 6 of Table I)

Stage 1

This describes the preparation of the ketone intermediate of structure:

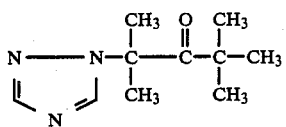

To a suspension of sodium hydride (50% oil dispersion) (0.48 g, 0.010M) in dry dimethylformamide (10 mls) was added a solution of 2,2-dimethyl-4-(1,2,4-triazol-1-yl)-pentan-3-one (1.81 g, 0.010M) in dry dimethylformamide (10 mls). Iodomethane (1.56 g, 0.011M) was added dropwise and the resultant mixture stirred at room temperature for 72 hours. Methanol (1 ml) was added and the solvent removed in vacuo. The residue was partitioned between water and ether. The aqueous portion was further extracted with ether (2×). The combined ethereal extracts were washed with brine, dried (anhydrous MgSO4) and concentrated in vacuo to give an orange oil. Chromatography on silica using gradient elution (ethyl acetate (0–50%) in hexane) gave the product (0.58 g) as an orange oil.

NMR (CDCl3) 1.00 (9H, s), 1.81 (6H, s), 8.02 (1H, s), 8.29 (1H, s).

Stage 2

This describes the preparation of the final compound, of structure:

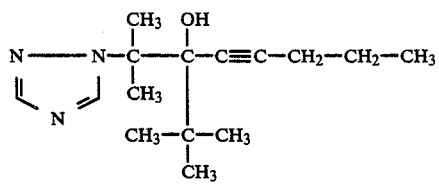

(Compound No 6 of Table I)

To a solution of pent-1-yne (0.25 g, 0.0037M) in dry tetrahydrofuran (10 mls) at 0° C., under nitrogen was added dropwise n-butyl lithium (2.3 mls of a 1.55M solution in hexane). The resulting solution was stirred for 15 minutes at 0° C. and then a solution of 2,2-dimethyl-4-methyl-4-(1,2,4-triazol-1-yl)-pentan-3-one (0.60 g, 0.0031M) in dry tetrahydrofuran (10 mls) was added dropwise. The resulting mixture was allowed to warm to room temperature over 2 hrs then heated at reflux for 1 hr. Methanol (1 ml) was added and the solvent removed in vacuo. The residue was partitioned between water and diethyl ether. The aqueous portion was further extracted with ether (2×). The combined ethereal layers were washed with brine, dried (anhydrous MgSO4) and then concentrated in vacuo to give a brown oil. Chromatography on silica eluting with diethyl ether gave the product (0.80 g) (73.5°–75.5° C.) as a white solid.

NMR (CDCl3) 0.95 (3H, t, J 7 Hz), 1.01 (9H, s), 1.2–1.6 (2H, cmplx), 1.85 (3H, s), 1.89 (3H, s) 2.11 (2H, t J 8 Hz), 4.80 (1H, s) 7.94 (1H, s), 8.23 (1H, s).

IR (nujol) 2500–3500 (strong) 2220 (weak) cm$^{-1}$.

m/e: no. M$^+$, 248, 206, 111, 110, 96.

Analysis: $C_{15}H_{25}N_3O$ requires: C, 68.40; H, 9.57; N, 15.95%. found: C, 68.57; H, 9.43; N, 15.84%.

EXAMPLE 6

This Example illustrates the preparation of the compound of structure:

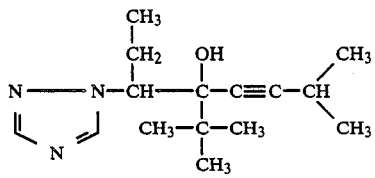

(Compound No 7 of Table I)

Using a method similar to those described in Examples Nos 1–5, using the appropriate reactants, the title compound was obtained as a single isomer m.pt. 129°–131.5° C. (white solid).

NMR (CDCl3) 0.66 (3H, t, J 8 Hz), 0.83 (9H, s), 1.20 (6H, d J 8 Hz), 2.0–2.9 (3H, cmplx), 3.32 (1H, s), 4.42 (1H, dd, J 8, 4 Hz), 7.96 (1H, s), 8.22 (1H, s).

IR (nujol) 2500–3500 (strong), 2220 (weak) cm$^{-1}$.

m/e: no. M$^+$, 248, 206, 111, 82.

Analysis: $C_{15}H_{25}N_3O$ requires: C, 68.40; H, 9.57; N, 15.95%. found: C, 68.50; H, 9.19; N, 15.98%.

EXAMPLE 7

This Example describes the preparation of the compound having the structure:

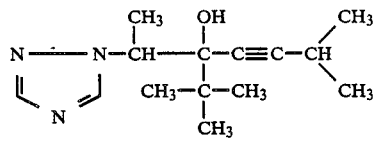

(Compound No 5 of Table I)

Using a method similar to those described in the preceding examples and using the appropriate reactants, the title compound was obtained as a 89:11 mixture of isomers, m.pt. 101°–102° C. (white solid).

NMR (CDCl3) 0.91 (9H, s), 1.18 (6H, d J 8 Hz), 1.74 (3H, d, (major isomers J 8 Hz), 2.60 (1H, heptet J 8 Hz), 3.37 (1H, s), 4.76 (1H, q J 8 Hz), 7.92 (1H, s), 8.24 (1H, s).

IR (nujol) 2500–3500 (strong), 2230 (weak) cm$^{-1}$.

m/e: no. M$^+$, 234, 192, 97, 82.

EXAMPLE 8

This Example illustrates the preparation of Compound No. 146 of Table I having the structure

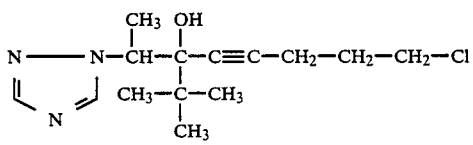

To a solution of 5-chloro-1-pentyne (1.4 g, 13.7 mmol) in dry THF (20 ml), at 0° C. under nitrogen, was added n-butyllithium (8.8 ml of a 1.5 molar solution in hexane). The reaction mixture was stirred for 5 minutes then cooled to −70° C. To the mixture was added dropwise a solution of 2,2-dimethyl-4-(1,2,4-triazol-1-yl)penten-3-one (2 g, 11 mmol) in THF (10 ml). The reaction mixture was stirred for 25 minutes then warmed to room temperature, quenched with ammonium chloride solution and partitioned between ethyl acetate and water. The aqueous portion was further extracted with ethyl acetate, then the combined organic extracts were washed with water and brine, dried over magnesium sulphate and concentrated in vacuo to give a yellow solid. Column chromatography of the crude product on silica gel, eluting with diethyl ether (20–100%) in petrol, afforded the title compound as a white solid (2.4 g) (mp. 89°–93° C.).

NMR (CDCl₃, 270 MHz) δ: 0.9 (9H, s); 1.76 (3H, d); 2.0 (2H, complex); 2.46 (2H, t); 3.68 (3H, complex); 4.76 (1H, complex); 7.92 (1H, s); 8.24 (1H, s).

m/e: No. M⁺, 226, 98, 97, 82, 69, 57.

Analysis $C_{14}H_{22}N_3O$, Cl, requires C, 59.25; H, 7.8; N, 14.81; Cl, 12.49%. found C, 59.55; H, 7.70; N, 14.92; Cl, 12.47%.

IR (nujol) 3050–3500, 2230 cm⁻¹.

EXAMPLE 9

This Example illustrates the preparation of the compound having the structure:

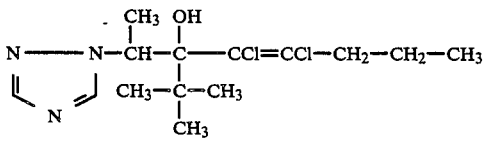

(Compound No. 117 of Table I)

by the addition of chlorine to compound No. 4 of Table I. To a solution of Compound No. 4 of Table I (0.87 g, 3.5 mmol) in chloroform (50 ml) at room temperature was added, portionwise, a solution of chlorine in chloroform (excess). The reaction mixture was stirred for 3 hours while being illuminated by a 60 watt lamp, then left at room temperature overnight. The solution was evaporated to give a yellow oil. Column chromatography of the crude product on silica gel eluting with diethyl ether (20–80%) in petrol gave the product as a mixture of cis and trans dichloroalkenyl compounds as a yellow gum (0.35 g). Trituration of the gum with petrol gave a white solid (mp. 95°–98½° C.). Data given is for a mixture of isomers.

NMR (CDCl₃, 270 MHz) 0.77 (minor isomer) and 0.84 (major isomer) 9H, s); 1.0 (3H, complex); 1.5 (3H, complex); 1.7 (2H, complex); 2.7 (2H, complex); 4.04 (1H, s); 5.4 (major isomer) and 6.1 (minor isomer (1H, complex); 7.9 (1H, s); 8.35 (1H, s).

(Except where stated nmr signals for the isomers overlap).

m/e: No. M⁺, 262, 167, 165, 129, 97, 91, 82, 70. IR (nujol) 3050–3550, 1600 cm⁻¹.

EXAMPLE 10

This Example illustrates the preparation of the compound of structure

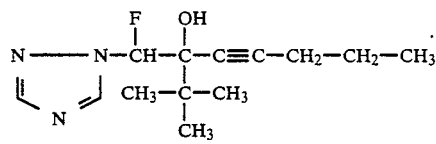

(Isomer A, compound No. 137 of Table I
Isomer B, compound No. 138 of Table I)

To a solution of 1-pentyne (2.4 ml, 0.024 mole) in dry THF (40 ml), at −30° C. under nitrogen, was added n-butyllithium (16 ml of a 1.5 molar solution in hexane) and the mixture stirred for 15 minutes. Chlorotitanium triisopropoxide (24 ml of a 1.0 molar solution in hexane) was added and the reaction mixture was stirred for 15 minutes, then cooled to −70° C. To the reaction mixture was added slowly a solution of 2,2-dimethyl-4-(1,2,4-triazol-1-yl)-4-fluoro-butan-3-one (prepared as described in EP 0116262) (4 g, 0.022 mole). The reaction mixture was allowed to warm to room temperature, then quenched with saturated NH₄Cl solution. The reaction mixture was partitioned between ethyl acetate and NH₄Cl solution. The aqueous portion was further extracted with ethyl acetate then the combined organic extracts were washed with water and brine, dried over MgSO₄ and concentrated in vacuo to give a yellow oil (5.3 g). Column chromatography of the crude product on silica gel eluting with diethyl ether (20–50%) in petrol gave the product as a mixture of isomers (1:1) (B 4.23 g). Trituration with diethyl ether and petrol gave isomer A as a white solid (1.05 g, mp. 73°–77° C.). Column chromatography of the residue on silica gel eluting with ethyl acetate (10–30%) in petrol gave isomer B as a colourless oil (0.67 g) plus some mixed fractions.

Isomer A

NMR (CDCl₃, 90 MHz): 0.85 (3H, t); 1.2 (9H, s); 1.3 (92H, complex); 2.04 (2H, t); 4.05 (1H, s); 6.08 6.6 (1H, d); 8.0 (1H, s); 8.56 (1H, s).

m/e: No. M⁺ 196, 153, 128, 10, 79, 70, 57.

IR (nujol) 3050–3550, 2240 cm⁻¹.

Analysis: $C_{13}H_{20}F,N_3O$, requires: C, 61.64; H, 7.96; N, 16.59%. found: C, 61.74; H, 8.39; N, 16.86%.

Isomer B

NMR (CDCl₃, 90 MHz): 1.0 (3H, t); 1.16 (9H, s); 1.6 (2H, complex); 2.15 (2H, t); 3.56 (1H, s); 6.1, 6.6 (1H, d); 7.93 (1H, s). 8.62 (1H, s).

m/e: No. M⁺ 196, 153, 128, 101, 100, 73, 70, 57.

IR (film) 3040–3550, 2240 cm⁻¹.

Analysis: $C_{13}H_{20}F,N_3O$ requires: C, 61.64; H, 7.96; N, 16–59%. found: C, 61.42; H, 7.90; N, 16.15%.

EXAMPLE 11

This Example illustrates the preparation of the compound of formula

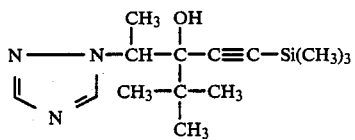

(Isomer A, compound No. 143 of Table I,
Isomer B, compound No. 144 of Table I).

To a solution of trimethylsilylacetylene (4.0 ml, 28 mmol) in dry THF (30 ml), under nitrogen at −10° C., was added n-butyl lithium (18.5 ml of a 1.5 molar solution in hexane). The reaction mixture was stirred for 30 minutes then added slowly to a solution of 2,2-dimethyl-4-(1,2,4-triazol-1-yl)pentan-3-one (5.0 g 28 mmol) in THF (25 ml) under nitrogen at −10° C. The reaction mixture was stirred for 30 minutes, warmed to room temperature overnight then partitioned between diethyl ether and water. The aqueous portion was further extracted with ether then the combined ethereal extracts were washed with water and brine, dried over MgSO4 and evaporated to dryness to give a yellow solid (7.85 g) which contained the product as a mixture of isomers (7:1). Trituration with petrol gave the major isomer A as a white solid (4.4 g) (mp. 104°-5°-107° C.). Column chromatography of the concentrated mother liquor on silica gel gave a small quantity of the minor isomer B as a white solid (mp. 91°-94° C.).

Isomer A

NMR (CDCl3, 90 MHz) δ: 0.23 (9H, s); 0.95 (9H, s); 1.76 (3H, d); 3.7 (1H, s); 4.76 (1H, q); 7.9 (1H, s); 8.22 (1H, s)
m/e: No. M+, 222, 97, 82, 73.
IR (nujol) 3030-3500, 2170 cm−1.
Analysis: $C_{14}H_{25}N_3O,Si$, requires: C, 60.17; H, 9.02; N, 15.04%. found: C, 60.43; H, 9.06; N, 15.23%.

Isomer B

NMR (CDCl3, 270 MHz) δ: 0.12 (9H, s); 1.0 (9H, s); 1.66 (3H, d); 3.28 (1H, s); 5.73 (1H, q); 7.91 (1H, s); 8.28 (1H, s).
m/e: No. M+, 222, 183, 154, 99, 97, 82, 75, 73, 57.
IR (nujol) 3050-3500, 2170 cm−1.
Analysis: $C_{14}H_{25}N_3O$Si requires: C, 60.17; H, 9.02; N, 15.04%. found: C, 60.11; H, 9.40; N, 15.15%.

EXAMPLE 12

This Example illustrates the preparation of the compound of the formula

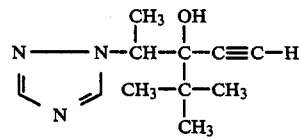

(Compound No. 142 of Table I)

To a solution of the product of Example 11 (isomer A-compound No. 143 of Table I) (4.0 g, 14 mmol) in methanol (40 ml) at room temperature was added potassium carbonate (0.25 g, 1.8 mmol). The reaction mixture was stirred at room temperature for 2 hours then left overnight. The reaction mixture was concentrated in vacuo and the residue partitioned between dichloromethane and water. The aqueous portion was neutralised with glacial acetic acid, then further extracted with dichloromethane. The combined organic extracts were washed with water and brine, dried over MgSO4 and evaporated to dryness to give a white solid (2.8 g) (mp. 133°-136° C.).

NMR (CDCl3, 270 MHz)δ: 0.92 (9H, s); 1.75 (3H, d); 2.56 (1H, s); 4.11 (1H, s); 4.8 (1H, q); 0.92 (1H, s); 8.26 (1H, s).
IR (nujol) 3030-3450, 3260, 3120, 2110 cm−1.
m/e: 208 (MH+) 182, 150, 111, 97, 82, 70, 57, 43.
Analysis: $C_{11}H_{17}N_3O$ requires: C, 63.74; H, 8.27; N, 20-27%. found: C, 63.59; H, 7.83; N, 20.29%.

EXAMPLE 13

This Example illustrates the preparation of the compound of formula

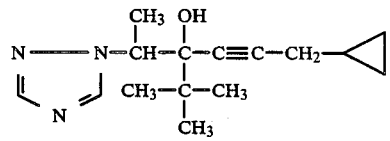

(Compound No. 145 of Table I)

To liquid ammonia (approx. 50 ml) at −60° C. was added a small piece of lithium (from 0.20 g, 29 mmol) followed by a spatula tip full of ferric nitrate. The remaining lithium was added gradually and the reaction mixture stirred for 15 minutes until the blue colour had been discharged and a grey suspension was left. To the reaction mixture was added a solution of the product of Example 12—compound No. 142 of Table I (2.0 g, 9.65 mmol) in THF (16 ml) and the mixture stirred for 45 minutes, allowing the bath temperature to rise to −45° C. The mixture was cooled to −60° C., cyclopropylmethyl bromide (1.9 ml, 19 mmol) was added then the reaction mixture was allowed to warm to room temperature overnight. The reaction mixture was partitioned between ethyl acetate and 20% NH4Cl solution, then the aqueous portion was further extracted with ethyl acetate. The combined organic extracts were washed with water and brine, dried over MgSO4 and concentrated in vacuo to give a yellow solid (2.3 g). Column chromatography on silica gel eluting with diethyl ether 10-60% in petrol gave the title compound as a white solid (0.93 g) (mp. 111°-114½° C.).

NMR (CDCl3, 90 MHz)δ: 0.3 (2H, complex); 0.5 (2H, complex); 0.8 (1H, complex); 0.94 (9H, s); 1.76 (3H, d); 2.3 (2H, d); 3.65 (1H, s); 4.75 (1H, q); 7.92 (1H, s); 8.28 (1H, s).
m/e: No. M+, 204 165, 136, 107, 97, 82, 57.
IR Nujol 3050-3450, 2230 cm−1.

EXAMPLE 14

This Example illustrates the preparation of the compound of formula

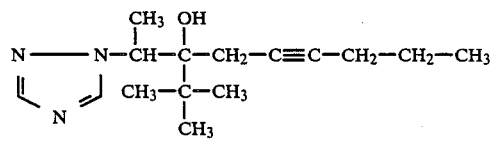

(Isomer A, Compound No. 131 of Table I
Isomer B, Compound No. 132 of Table I)

Stage 1

Preparation of

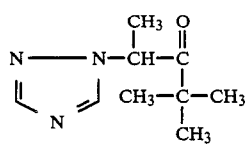

To a solution of 2,2-dimethylethyl-4-(1,2,4-triazolyl-1-yl)-butan-3-one (50.1 g, 0.3M) in tetrahydrofuran (300 ml) was added a solution of sodium hydroxide (24 g, 0.6M) in water (60 mls). After 10 minutes a solution of methyliodide (42.6 g, 0.3M) in tetrahydrofuran (50 ml) was added dropwise. The resultant solution was then heated reflux for 2 hours, then cooled. The tetrahydrofuran was removed in vacuo and the residue partitioned between water and diethyl ether. The aqueous was further extracted with ether (2×). The combined ether extracts were washed with water and brine, dried (MgSO4) filtered and concentrated in vacuo to give a pale orange oil (47.2 g) which crystallised on standing. Recrystallisation of a small sample from ether/petrol gave the 2,2-dimethyl-4-(1,2,4-triazoly-1-yl)pentan-3-one as a white solid, melting point 34°–37° C.

NMR (CDCl3) 1.28 (9H, s); 1.7 (3H, dJ8 Hz); 5.74 (1H, q,J8 Hz); 7.97 (1H, s); 8.38 (1H, s).

IR (film) 3130, 1720 cm$^{-1}$.

m/e: 181, 166, 82, 57.

Analysis: $C_9H_{15}N_3O$ requires: C, 59.72; H, 8.24; N, 23.20. found: C, 59.95; H, 8.33; N, 23.06.

Stage 2

Preparation of

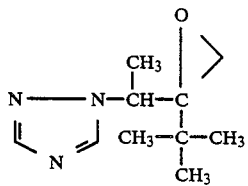

To a solution of 2,2-dimethyl-4-(1,2,4-triazolyl-1-yl)-pentan-3-one prepared in stage 1 (10 g, 0.055 mol) in dimethyl sulphoxide (150 ml) was added, in one portion, powdered potassium hydroxide (7.3 g, 0.11 mol) and the resulting mixture was stirred for 2½ hours at room temperature. The mixture was then partitioned between diethyl ether and water, and the aqueous fraction further extracted with diethyl ether and ethyl acetate. The combined organic were washed with water, saturated sodium bicarbonate solution and brine, dried over sodium sulphate and concentrated in vacuo to give the title compound as a mixture of diastereoisomers as a yellow oil (6.75 g). Column chromatography of a portion of the product (2.0 g on silica gel, eluting with diethyl ether 10–90% in petrol afforded isomer A (0.27 g), isomer B (0.35 g) and a mixed fraction (1.2 g).

Isomer A

NMR (CDCl3, 100 MHz)δ: 1.00 (9H, s); 1.50 (3H, d); 2.44 (1H, d); 2.86 (1H, d); 5.10 (1H, q); 6.98 (1H, s); 8.16 (1H, s).

m/e: No. m+, 180, 126, 110, 96, 8, 3, 82.

Isomer B

NMR (CDCl3, 100 MHz)δ: 0.94 (9H, s); 1.50 (3H, d); 2.84 (2H, s); 5.88 (1H, q); 7.92 (1H, s); 8.30 (1H, s).

m/e: No. M+, 180, 111, 110, 96, 82.

Stage 3

To a stirred solution of ethyl magnesium bromide (34 ml of a 3.0M solution in diethyl ether) in dry tetrahydrofuran (70 ml), under nitrogen at room temperature, was added pent-1-yne (10 ml, 0.1 mol). When the initial refluxing had subsided the mixture was heated under reflux for 20 minutes then cooled to room temperature. To the reaction mixture was added a solution of the epoxide described in stage 2 (10 g, 0.05 mol) in dry tetrahydrofuran (50 ml). The mixture was heated under reflux for 3½ hours, then cooled and partitioned between ethyl acetate and water. The aqueous fraction was further extracted with ethyl acetate, and the combined organic extracts washed with water and brine, dried over magnesium sulphate and concentrated in vacuo to give the product as a mixture of diastereoisomers, as a brown oil. Repeated column chromatography of the crude product on silica gel, eluting with diethyl ether 10–70% in petrol afforded isomer A (5.3 g) as a pale yellow oil which solidified on standing to give a waxy solid (m.pt 47°–51° C.) and isomer B (1.8 g) as a white solid (m.pt 83°–86° C.).

Isomer A

NMR (CDCl3, 270 Mhz)δ: 0.86 (9H, s); 0.96 (3H, t); 1.5 (2H, m); 1.60 (3H, d); 2.1 (2H, m); 2.60 (2H, q); 3.84 (1H, s); 4.96 (1H, q); 7.94 (1H, s); 8.20 (1H, s).

m/e: 262, 248, 235, 206, 182, 137, 96, 81.

IR (film) 3150–3650, 3125 cm$^{-1}$.

Analysis: $C_{15}H_{25}N_3O$ requires: C, 68.4; H, 9.57; N, 15.95%. found: C, 68.01; H, 9.74; N, 15.49%.

Isomer B

NMR (CDCl3, 270 MHz)δ: 1.0 (3H, t); 1.08 (9H, s); 1.52 (2H, m); 1.66 (3H, d); 1.7 (1H, m); 2.16 (3H, m); 2.7 (1H, d); 3.60 (1H, s); 4.98 (1H, q); 7.96 (1H, s); 8.10 (1H, s).

m/e: 248, 235, 206, 183, 182, 137, 96.

IR (film) ν 3150–3500, 3125 cm$^{-1}$.

Analysis: $C_{15}H_{25}N_3O$ requires: C, 68.4; H, 9.57; N, 15.95%. found: C, 68.61; H, 9.50; N, 15–65%.

EXAMPLE 15

This Example illustrates the preparation of the compound of formula

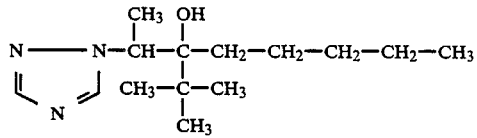

In dry apparatus under nitrogen, n-butyllithium (20.5 mls of 1.5 mol in hexane, 0.031 mol) was gradually added dropwise with stirring to a suspension of cuprous iodide (2.93 g, 0.0154 mol) in dry Et2O (50 mls) maintained at −50° C. The mixture was stirred at −50° C. for 20 minutes then a solution of the epoxide prepared in stage 2 of Example 14—isomer A (1.5 g, 0.0077 mol) in dry Et2O (15 mls) was gradually added dropwise with stirring at below −50° C. The mixture was stirred at −50° C. for 2 hours and allowed to warm to 15° C. Aqueous ammonia (15%) was cautiously added with stirring and cooling and filtered. The organic layer was separated and the aqueous layer was re-extracted with ethyl acetate. Combined organic layers were washed with aqueous ammonium chloride (20%) then water and brine. Dried (anhydrous MgSO₄), decolourised with activated charcoal and concentrated in vacuo to leave an orange oil. Chromatography using silica gel and CH₂Cl₂ then Et₂O as eluent gave the title compound as a pale yellow oil, (1.60 g, 82%).

NMR (CDCl₃): 0.86 (3H, t); 0.98 (9H, s); 1.00–1.50 (8H, complex); 2.66 (3H, d); 3.30 (1H, s); 4.71 (1H, quartet); 7.94 (1H, s); 8.19 (1H, s).

IR: 3650–3050, 3150.

m/e: MH+ at 254 due to self C.I., 236, 196, 182, 157, 97, 82.

Analysis: C₁₄H₂₇N₃O requires: C, 66.36, H, 10.74; N, 16.58%. found: C, 66.54; H, 10.66; N, 16.42%.

EXAMPLE 16

This Example illustrate the preparation of the compound of formula

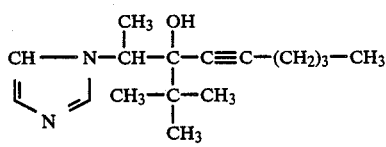

Compound No. 73 of Table I

Stage 1

Preparation of 2,2-dimethyl-4-(1H-imidazol-1-yl)pentan-3-one

To a stirred solution of 4,4-dimethyl-1-(1H-imidazol-1-yl)butan-2-one (4.0 g, 24.1 mmol) in dry THF (30 ml) at −78° C. was added a solution of lithium di-isopropylamine in THF [prepared from di-isopropylamine (2.4 g) and n-butyl lithium (9.6 ml of 2.5M, 24.1 mmol) in dry THF (20 ml)]. After 30 minutes, methyl iodide (3.42 g, 24.1 mmol) was added and the solution allowed to warm to room temperature over 3 hours. The reaction mixture was then poured into water and extracted with ether (2×250 ml). The ethereal layer was collected, dried over anhydrous magnesium sulphate and the solvent removed. Chromatography of the resulting gum gave the product as a clear gum (1.76 g, 41%), bp. 170° C. at 0.5 mmHg (Found: C, 63.4; H, 8.9; N, 14.8. C₁₀H₁₆N₂O requires C, 66.6; H, 8.95; N, 15.55%); ν IR 3400, 3100, 2950, 1705, 1475, 1370, 1230, 990, 910, 820, 740, 680 cm⁻¹.

(90 MHz; CDCl₃)δ: 1.2 (9H, s); 1.58 (3H, d, J 7 Hz); 5.32 (1H, q, J 7 Hz); 7.04 (2H, s); 7.56 (1H, s).

m/z 180 (M+), 165, 95 (100%), 85, 68, 57, 41.

Stage 2

Preparation of 2,2-dimethyl-3-(1-[1H-imidazol-1-yl]ethyl)non-4-yne-3-ol

To a stirred solution of hex-1-yne (0.61 g, 7.5 mmol) in dry THF (30 ml) was added n-butyl lithium (3 ml of 2.6M, 7.5 mmol) at −78° C. under a nitrogen atmosphere. After 15 minutes, a solution of 2,2-dimethyl-4-(1H-imidazol-1-yl)-pentan-3-one (1.26 g, 7 mmol) in dry THF (30 ml) was added dropwise. Upon complete addition the mixture was allowed to warm to room temperature and stirred for 18 hours. The reaction mixture was then poured onto ice and extracted with ether (2×250 ml). The ethereal solution was washed with saturated brine solution then dried over anhydrous magnesium sulphate and the solvent removed. The resulting yellow oil was chromatographed (silica gel, petrol/diethyl ether elution) to give the product as a white solid (1.39 g, 76%), mp. 57–59% (Found C, 72.2; H, 10.1; N, 10.8. C₁₆H₂₆N₂O requires C 73.3; H, 9.9; N, 10.7%); IR 2950, 1460, 1360, 1270, 1220, 1080 980, 920, 810, 730, 660 cm⁻¹.

NMR (90 MHz; CDCl₃) 0.9 (3H, t, J 6.3 Hz), 1.0 (9H, s); 1.3–1.56 (4H, m); 1.65 (3H, d, J 6.3 Hz); 2.26 (2H, m); 3.06 (1H, s); 4.57 (1H, q, J 6.3 Hz); 6.98 (1H, s); 7.08 (1H, s); 7.6 (1H, s).

m/z 263, 262 (M+), 261, 205, 167, 111, 96 (100%), 69, 43.

EXAMPLE 17

This Example illustrates the preparation of the compound

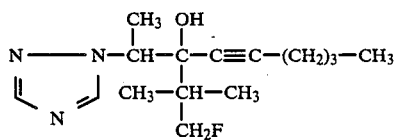

Isomer A Compound No. 70A of Table I
Isomer B Compound No. 70B of Table I

Preparation of 2,2-dimethyl-1-fluoro-3-(1[1H-1,2,4-triazolyl]ethyl)non-4-yne-3-ol To a stirred solution of hex-1-yne (1.23 g, 15 mmol) in dry THF (40 ml) was added n-butyl lithium (6 ml of 2.6M, 15 mmol) at −78° C. under a nitrogen atmosphere. After 15 minutes, a solution of 2,2-dimethyl-1-fluoro-4-(1H-1,2,4-triazol-1-yl)-pentan-3-one (2.5 g, 13 mmol) in dry THF (20 ml) was added dropwise. Upon complete addition the mixture was allowed to warm to room temperature and stirred for 18 hours. The reaction mixture was then poured onto ice and extracted with ether (2×250 ml). The ethereal solution was washed with saturated brine solution then dried over anhydrous magnesium sulphate and the solvent removed. The resulting yellow oil was chromatographed (silica gel, petrol/diethyl ether elution) to give a yellow gum (2.0 g, 56.5%) which was a mixture of the RS/SR and the RR/SS forms. This gum was then purified by preparative chromatography to give the pure RS/SR form as a white solid (0.24 g, 6.8%), mp. 72°–74° C. (Found: C, 63.5; H, 9.0; N, 15.0C₁₅H₂₄FN₃O requires C, 64.1; H, 8.5; N, 14.95%); IR 3200, 2950, 2225, 1360, 1280, 1200, 1140, 1000, 870, 680 cm⁻¹; NMR (90 MHz; CDCl₃) 0.8 (6H, s); 0.9 (3H, t, J 7 Hz); 1.2–1.56 (4H, m); 1.72 (3H, d, J 6.3 Hz); 2.24 (2H, m); 3.8 (1H, br); 4.36 (2H, dq, J 46.8 and 6.3 Hz), 4.8 (1H, q, J 6.3 Hz); 7.95 (1H, s); 8.24 (1H, s); m/z 282 (M+H+) 206, 185, 109, 97 (100%), 82. The RR/SS component could not be isolated in a pure state thus, a 1:1 mixture of the RS/SR and RR/SS forms was obtained as a yellow oil (0.34 g, 9.6%); NMR (90 MHz; CDCl₃) 0.8 (6H, s); 0.92 (3H, t, J 7 Hz); 1.2–1.56 (4H, m); 1.66 (3H, d, J 6.3 Hz); 2.13 (2H, m); 3.8 (1H, br); 4.36 (2H, dq, J 46.8 and 6.3 Hz), 4.76 (1H, q, J 6.3

Hz); 7.93 (1H, s); 8.26 (1H, s); m/z 282 (M+H+), 206, 185, 109, 97 (100%), 82.

EXAMPLE 18

This Example illustrates the preparation of the compound

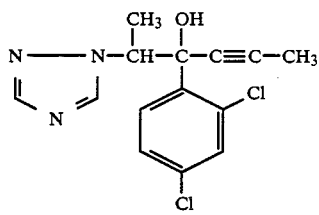

Compound No. 74 of Table I

Stage 1

The preparation of 1-(2,4-dichlorophenyl)-2-bromo-propan-1-one

A solution of 1-(2,4-dichlorophenyl)propan-1-one (10 g) in ethyl acetate (50 ml) and chloroform (50 ml) was refluxed under argon, and powdered cupric bromide (22 g) was added in small portions over 4½ hours. The green colour from each portion was allowed to disappear before the next portion was added. The resultant mixture was stirred under reflux for a further 1 hour, left undisturbed at room temperature overnight and then refluxed for a further 5 hours. The mixture was cooled, filtered and the colourless solid cuprous bromide washed with chloroform (25 ml). The combined filtrate and washings were concentrated in vacuo and the oily residue was dissolved in diethyl ether (200 ml), washed with 10% sodium bicarbonate (2×50 ml) and water (50 ml), then dried over anhydrous magnesium sulphate. Concentration in vacuo gave 13.65 g (98%) of an orange liquid.

IR 3090 cm$^{-1}$, 2970 cm$^{-1}$, 2925 cm$^{-1}$, 2850 cm$^{-1}$, 1705 cm$^{-1}$.

NMR ($\delta$): 1.86 (3H, d); 5.16 (1H, q); 7.24 (1H, dd); 7.30 (1H, d); 7.44 (1H, d).

Stage 2

The preparation of 5-bromo-4-(2,4-dichlorophenyl)-4-hydroxy-hex-2-yne

A solution of 3M ehtyl magnesium bromide in diethyl ether (19.8 ml) was added dropwise over 25 minutes, to dry THF (250 ml) through which 1-propyne was constantly bubbled at 0° C. under argon. After complete addition, the 1-propyne was bubbled through the mixture for a further 30 minutes and then stopped. A solution of 1-(2,4-dichlorophenyl)-2-bromo-propan-1-one (15.95 g) in dry THF (50 ml) was added dropwise to the mixture at 0°-5° C. over 30 minutes. The resultant pale yellow solution was stirred at 0° C. for 35 minutes. Aqueous ammonium chloride (10%, 200 ml) was added and the mixture extracted with diethyl ether (2×200 ml). The combined ether extracts were washed with water until neutral, dried over anhydrous magnesium sulphate and concentrated in vacuo to give, 18.42 g, of a pale yellow oil. The crude material was taken through to the next stage.

NMR ($\delta$): 1.8 (3H, d); 1.92 (3H, s); 3.14 (1H, s); 5.14 (1H, q); 7.24 (1H, dd); 7.38 (1H, d); 7.8 (1H, d).

Stage 3

The preparation of 4-(2,4-dichlorophenyl)-4-hydroxy-5-(1,2,4-triazol-1-yl)-hex-2-yne A suspension of sodium hydride (2.54 g) in dry dimethylsulphonyl (200 ml) was stirred at room temperature under argon and 1,2,4-triazol 21.9 g) was added in portions over 10 minutes, followed by further stirring for 10 minutes. A solution of 5-bromo-4-(2,4-dichlorophenyl)-4-hydroxy-hex-2-yne (17 g) in dry DMSO (50 ml) was added over 15 minutes. The resultant solution was heated at 100° C. for about 100 hours. Concentrated brine solution (200 ml) was added and the mixture extracted with ethyl acetate (3×150 ml). The extracts were combined, washed with water until neutral, dried over anhydrous magnesium sulphate and the solvent removed in vacuo to give 14.38 g of a brown solid. This solid was purified by flash chromatography, eluted with portions of ethyl acetate (50-100%) in hexane). Fractions containing the fastest running major triazole-active spot on thin-layer chromatography were combined to give 2.91 g (18%) of a white solid.

Mpt. 166.6°-169.4° C.

IR 3100 cm$^{-1}$, 2230cm$^{-1}$.

NMR ($\delta$): 1.78 (3H, d); 1.88 (3H, s); 4.68 (1H, s); 5.58 (1H, q); 7.04 (1H, dd); 7.34 (1H, d); 7.4 (1H, d); 7.74 (1H, s); 7.88 (1H, s).

EXAMPLE 19

An emulsifiable concentrate was made up by mixing the ingredients, and stirring the mixture until all the constituents were dissolved.

| | |
|---|---|
| Compound of Example 1 | 10% |
| Ethylene dichloride | 40% |
| Calcium dodecylbenzenesulphate | 5% |
| "Lubrol" L | 10% |
| "Aromasol" H | 35% |

EXAMPLE 20

A composition in the form of grains readily dispersible in a liquid, eg. water, was prepared by grinding together the first three ingredients in the presence of added water andd then mixing in the sodium acetate. The resultant mixture was dried and passed through a British Standard mesh sieve, size 44-100, to obtain the desired size of grains.

| | |
|---|---|
| Compound of Example 1 | 50% |
| "Dispersol" T | 25% |
| "Lubrol" APN5 | 1.5% |
| Sodium acetate | 23.5% |

EXAMPLE 21

The ingredients were all ground together to produce a powder formulation readily dispersible in liquids.

| | |
|---|---|
| Compound of Example 1 | 45% |
| "Dispersol" T | 5% |
| "Lissapol" NX | 0.5% |
| "Cellofas" B600 | 2% |
| Sodium acetate | 47.5% |

EXAMPLE 22

The active ingredient was dissolved in a solvent and the resultant liquid was sprayed on to the granules of China clay. The solvent was then allowed to evaporate to produce a granular composition.

| Compound of Example 1 | 5% |
|---|---|
| China clay granules | 95% |

EXAMPLE 23

A composition suitable for use as a seed dressing was prepared by mixing the three ingredients.

| Compound of Example 1 | 50% |
|---|---|
| Mineral oil | 2% |
| China clay | 48% |

EXAMPLE 24

A dusting powder was prepared by mixing the active ingredient with talc.

| Compound of Example 1 | 5% |
|---|---|
| Talc | 95% |

EXAMPLE 25

A Col formulation was prepared by ball-milling the substituents set out below and then forming an aqueous suspension of the ground mixture with water.

| Compound of Example 1 | 40% |
|---|---|
| "Dispersol" T | 10% |
| "Lubrol" APN5 | 1% |
| Water | 49% |

EXAMPLE 26

A dispersable powder formulatin was made by mixing together the ingredients set out below and then grinding the mixture until all were thoroughly mixed.

| Compound of Example 1 | 25% |
|---|---|
| "Aerosol" OT/B | 2% |
| "Dispersol" A.C. | 5% |
| China clay | 28% |
| Silica | 40% |

EXAMPLE 27

This Example illustrates the preparation of a dispersible powder formulation. The ingredients were mixed and the mixture then ground in a communication mill.

| Compound of Example 1 | 25% |
|---|---|
| "Perminal" BX | 1% |
| "Dispersol" T | 5% |
| Polyvinylpyrrolidone | 10% |
| Silica | 25% |
| China clay | 34% |

EXAMPLE 28

The ingredients set out below were formulated into a dispersible powder by mixing then grinding the ingredients.

| Compound of Example 1 | 25% |
|---|---|
| "Aerosol" OT/B | 2% |
| "Dispersol" A | 5% |
| China clay | 68% |

In Examples 8 to 17 the proportions of the ingredients given are by weight. The remaining compounds of Table I were all similarly formulated as per Examples 8 to 17.

There now follows an explanation of the compositions or substances represented by the various Trade Marks mentioned above.

LUBROL L: a condensate of nonyl phenol (1 mole) with ethylene oxide (13 moles)

AROMASOL H: a solvent mixture of alkylbenzenes

DISPERSOL T & AC: a mixture of sodium sulphate and a condensate of formaldehyde with sodium naphthalene sulphonate LUBROL APN5: a condensate of nonyl phenol (1 mole) with naphthalene oxide (5.5 moles)

CELLOFAS B600: a sodium carboxymethyl cellulose thickener

LISSAPOL NX: a condensate of nonyl phenol (1 mole) with ethylene oxide (8 moles)

AEROSOL OT/B: a sodium alkyl naphthalene sulphonate

EXAMPLE 29

Whole Plant Screen (1)

Compound numbers 3-8, 40, 156, 150, 151 of Table I were tested o the whole plant screen. The use of whole plant in this context refers to entire plants as opposed to a partial screen or an enzyme screen. The compounds were tested for plant growth regulator activity against up to twelve plant species for various growth effects relevant to plant growth regulation.

Methodology

The plant species used in this screen are presented in Table III, with the leaf stage at which they were sprayed. Each chemical was applied at 4000 ppm (4 kg/ha in a 1000 l/ha field volume) using a tracksprayer and a SS8004E (Teejet) nozzle.

After spray, the plants were grown in a glasshouse with 25° C. day/22° C. night temperatures and supplementary lighting was supplied when necessary (from mercury vapour lamps), to provide an average 16 hour photoperiod. The exception to this were the temperate cereals, wheat and barley, which were grown in 16° C. day/13° C. night temperatures.

After 2-3 weeks in the glasshouse, depending on the time of year, the plants were visually assessed for morphological characteristics. Formulation blanks were used as controls to assess the plants. The results are presented in Table IV.

TABLE III

PLANT MATERIAL USED FOR WHOLE PLANT SCREEN

| Species | Code | Variety | Growth Stage at Treatment | No. Plants per 3" Pot | Compost Type |
|---|---|---|---|---|---|
| Barley | BR | Atem | 1-1.5 leaves | 4 | JIP* or PEAT |
| Wheat | WW | Timmo | 1-1.5 leaves | 1 | JIP OR PEAT |
| Maize | MZ | Earliking | 2¼ leaves | 1 | PEAT |
| Vines | VN | Ohanez + unspecified | 4 leaves | 1 | PEAT |
| Soya | SY | Amsoy | 1st trifoliate | 1 | JIP |
| Tomato | TO | Ailsa Craig | 1.5-2 leaves | 1 | PEAT |
| Lettuce | LT | Verpia | 3-4 leaves | 1 | PEAT |
| Sugar beet | SB | Amono | 2 leaves | 1 | PEAT |
| *Agrositis tenius* | AT | | cut to 2 cm | Grown in rows | |
| *Cynosurus cristatus* | CC | | 48 hours before | in plastic | PEAT |
| *Dacrylis glomerata* | DA | | treatment | punnets | |
| Radish | RA | Istar | seeds | 4 | PEAT |

JIP* = John Innes Potting Compost.

TABLE IV

| COMPOUND NO. | WW | BR | MZ | AT | CC | DA | SY | SB | LT | TO | VN | RA |
|---|---|---|---|---|---|---|---|---|---|---|---|---|
| 1 | 3GT | | 2GA | 3G | 3G | 3G | 3GT | | 2G | 3G | 2AG | 3G |
| 3 | 2GT | 1GT | 1 | 2 | 1 | 1 | 1AG | 1G | 1 | 1 | 2AT | — |
| 4 | 1GT | 1 | | 1 | 1 | 1 | 1T | 1G | | | 2AT | — |
| 5 | 2GT | 2GT | | | 1 | | 2G | G | | 1G | 2A | — |
| 6 | 1T | 1T | | 2 | 2 | 2 | 2GAT | 1G | 1G | 3G | 1GT | — |
| 7 | 2GT | 1 | | | | 1 | 1AG | | 1 | 2G | | — |
| 8 | 1T | 1T | | 1 | 1 | 1 | 1AG | | 1G | 1 | 1AT | — |
| 40 | 2GT | 1T | | 1G | 1G | | 3G | 2G | 1G | 3GT | 2G | — |
| 156 | 1GT | 1 | | * | * | | 2G | G | | 1G | | — |
| 150 | *2GT | 1T | | | | | 2G | 1G | G | 1G | | — |
| 151 | 1T | * | | | | | G | *G | 1 | 1G | 1G | — |

Key
Retardation 1-3 where 1 = 10-30% retardation
2 = *-60% retardation
3 = 61-100% retardation
Greening effect = G
Apical damage = A
Tillering or side shooting = T
Blank means less than 10% effect - indicates that the compound was not tested against this species

EXAMPLE 30

Whole Plant Screen (2)

Compound members indicated in Table VI were tested on an alternative whole plant screen (2). The compounds were tested for plant growth regulator activity against five species for various growth effects relevant to plant growth regulation.

Methodology

The plant species used in this screen are presented in Table V with the leaf stage at which they were sprayed. Each chemical was applied at 4000 ppm (4 kg/ha in a 1000 l/ha field volume) using a tracksprayer and a SS8004E (Teejet) nozzle.

After spray the plants were grown in a glasshouse with 25° C. day/22° C. night temperatures and supplementary lighting was supplied when necessary (from mercury vapour lamps), to provide an average 16 hour photoperiod. The exception to this were the temperate cereals, wheat and barley which were grown in 16° C. day/13° C. night temperatures.

After 2-6 weeks in the glasshouse, depending on the time of year, the plants were visually assessed for morphological characteristics. Formulation blanks were used as controls to assess the plants. The results are presented in Table VI.

TABLE V

PLANT MATERIAL USED FOR WHOLE PLAN SCREEN (2)

| Species | Code | Variety | Growth Stage at Treatment | No. Plants per 3" Pot | Compost Type |
|---|---|---|---|---|---|
| Barley | BR | Atem | 1-1.5 leaves | 4 | JIP* |
| Wheat | WW | Timmo | 1-1.5 leaves | 4 | JIP |
| Maize | MZ | Earliking | 2¼ leaves | 1 | PEAT |
| Apple | AP | Red Delicious | 4-5 leaves | 1 | JIP |
| Rice | RC | Ishikari | 2-2½ leaves | 4 | JIP |

JIP* = John Innes Potting Compost.

Key to Table VI

R = Retardation
G = Greening effect
A = Apical damage
T = Tillering or side shooting
I = Interligular or internodal length reduction
All effects are scored visually on a 1-3 basis where
1 = 10-30%
2 = 31-60%
3 = 61-100%
blank means less than 10% effect.

TABLE VI

| Compound No. | Species | R | G | A | T | I |
|---|---|---|---|---|---|---|
| 10 | WW | 2 | 1 | | 1 | 3 |
| | BR | 2 | | | | 3 |
| | RC | | | | | |

TABLE VI-continued

| Compound No. | Species | R | G | A | T | I |
|---|---|---|---|---|---|---|
| 13 | AP | | | | | |
| | MZ | 1 | | | | 1 |
| | WW | 2 | 1 | | | 2 |
| | BR | | | | | |
| | RC | | | | | |
| 14 | AP | | | | | |
| | MZ | | | | | |
| | WW | 1 | | | 1 | 1 |
| | BR | 1 | | | | 2 |
| | RC | | | | | |
| 15 | AP | | | | | |
| | MZ | 1 | | | | 1 |
| | WW | 1 | | | 2 | 1 |
| | BR | | | | | 1 |
| | RC | | | | 1 | |
| 17 | AP | | | | | |
| | MZ | | | | | |
| | WW | 1 | | | | 1 |
| | BR | 1 | | | | 2 |
| | RC | | | | | 1 |
| 18 | AP | | | | | |
| | MZ | 1 | | | | 1 |
| | WW | 2 | | | 1 | 3 |
| | BR | 1 | | | | 3 |
| | RC | 1 | | | 1 | 1 |
| 19 | AP | | | | | |
| | MZ | | | | | |
| | WW | 1 | 1 | | | 3 |
| | BR | 1 | | | | 2 |
| | RC | | | | | |
| 23a | AP | 3 | | | | 3 |
| | MZ | | | | | |
| | WW | 2 | 1 | | 1 | 2 |
| | BR | 1 | | | 1 | 2 |
| | RC | | | | 1 | |
| 23b | AP | 1 | | | | |
| | MZ | 1 | | | | 1 |
| | WW | 2 | 1 | | | 3 |
| | BR | 1 | | | | 1 |
| | RC | | | | | |
| 26 | AP | 1 | | | | 1 |
| | MZ | | | | | |
| | WW | 1 | | | 1 | 2 |
| | BR | 1 | | | | 3 |
| | RC | | | | 1 | |
| 29 | AP | 2 | 1 | 1 | | 2 |
| | MZ | | | | | |
| | WW | 1 | | | 2 | 1 |
| | BR | | | | | |
| | RC | | | | 1 | |
| 41 | AP | 2 | | | | 2 |
| | MZ | | | | | |
| | WW | 1 | | | 1 | 2 |
| | BR | | | | | 1 |
| | RC | | | | 1 | |
| | AP | 3 | | 2 | 2 | 3 |
| 45 | MZ | | | | | |
| | WW | 1 | 1 | | 1 | 3 |
| | BR | 1 | | | | 2 |
| | RC | | | | 2 | |
| 46 | AP | | | | | |
| | MZ | 1 | | | | 1 |
| | WW | 1 | | | 1 | 2 |
| | BR | | | | | |
| | RC | | | | | |
| 47 | AP | | | | | |
| | MZ | | | | | |
| | WW | 1 | | | 1 | 2 |
| | BR | | | | | 1 |
| | RC | | | | 1 | |
| | AP | 2 | | | | 3 |
| 51a | MZ | | | | | |
| | WW | 1 | 1 | | | 1 |
| | BR | | | | | |
| | RC | | | | | |
| | AP | 1 | | 1 | | 1 |
| | MZ | 1 | | | | 1 |
| 51b | WW | 2 | 2 | | | 3 |
| | BR | 2 | | | 1 | 1 |
| | RC | | | | | |
| 52 | AP | 1 | | | | 1 |
| | MZ | | 1 | 1 | | |
| | WW | | | | 2 | |
| | BR | | | | 2 | |
| | RC | | | | | |
| 154 | AP | | | | | |
| | MZ | | | | | |
| | WW | 1 | 1 | | 1 | 2 |
| | BR | 1 | | | | 1 |
| | RC | | | | | |
| 155 | AP | | | | | |
| | MZ | 1 | | | | 1 |
| | WW | 1 | | | 2 | 1 |
| | BR | 1 | | | | 1 |
| | RC | | | | 1 | |
| 74 | AP | | | | | |
| | MZ | 1 | | | | 1 |
| | WW | 2 | | | | 2 |
| | BR | 1 | 2 | | | 2 |
| | RC | 2 | 2 | | | 3 |
| 109 | AP | 2 | 1 | | | 2 |
| | MZ | 2 | 1 | 1 | | 3 |
| | WW | 1 | | | | 1 |
| | BR | 1 | | | | 2 |
| | RC | | | | 1 | |
| 111 | AP | | | | | |
| | MZ | 1 | | | | 1 |
| | WW | 2 | 1 | | 1 | 2 |
| | BR | | | | | |
| | RC | | | | | |
| 112 | AP | | | | | |
| | MZ | | | | | |
| | WW | 2 | 1 | | 1 | 2 |
| | BR | | | | | |
| | RC | | | | | |
| 119 | AP | | | | | |
| | MZ | | | | | 1 |
| | WW | 1 | | | | 2 |
| | BR | 1 | | | | 2 |
| | RC | 1 | 1 | | 2 | 3 |
| 120 | AP | | | | | |
| | MZ | | | | | |
| | WW | 1 | | | | 1 |
| | BR | 1 | | | | |
| | RC | 1 | 1 | | | 3 |
| 121 | AP | 3 | 1 | | | 3 |
| | MZ | | | | | |
| | WW | 2 | 1 | | | 3 |
| | BR | 2 | 1 | | | 2 |
| | RC | 2 | 1 | | | 2 |
| 140 | AP | 1 | | | | 3 |
| | MZ | | | | | |
| | WW | 1 | 1 | | 1 | 3 |
| | BR | | | | | 3 |
| | RC | 2 | | | 1 | 2 |
| 141 | AP | | | | | |
| | MZ | | | | | |
| | WW | 1 | | | | 3 |
| | BR | 1 | | | | |
| | RC | | | | | |
| 142 | AP | 3 | | | | 3 |
| | MZ | | | | | |
| | WW | 1 | 1 | | | 3 |
| | BR | 1 | | | | 3 |
| | RC | 2 | 1 | | 3 | 3 |
| 146 | AP | 3 | 1 | | | 3 |
| | MZ | | | 1 | | |
| | WW | 2 | 1 | | 1 | 3 |
| | BR | 2 | | | | 1 |
| | RC | 1 | | | 1 | 2 |
| 149 | AP | | | | | 1 |
| | MZ | | | | | |
| | WW | 2 | | | 1 | 2 |
| | BR | | | | | |
| | RC | | | | | |
| 131 | WW | 2 | 2 | | 1 | 3 |
| | BR | 1 | | | | |
| | RC | 2 | 1 | | 3 | 2 |

TABLE VI-continued

| Compound No. | Species | R | G | A | T | I |
|---|---|---|---|---|---|---|
|  | AP | 3 |  |  |  | 3 |
|  | MZ | 1 | 1 | 1 |  |  |
| 132 | WW | 2 | 2 |  | 1 | 3 |
|  | BR |  |  |  |  | 1 |
|  | RC | 2 | 1 |  | 2 | 2 |
|  | AP | 2 |  |  |  | 3 |
|  | MZ |  |  |  |  |  |
| 135 | WW | 2 | 1 |  | 1 | 3 |
|  | BR | 1 |  |  | 2 | 3 |
|  | RC | 2 | 1 |  |  | 3 |
|  | AP | 2 | 1 | 1 | 3 | 3 |
|  | MZ | 1 |  |  |  | 1 |
| 136 | WW | 2 | 1 |  | 1 | 3 |
|  | BR | 1 |  |  |  | 1 |
|  | RC |  |  |  | 1 |  |
|  | AP | 2 |  | 3 | 3 | 2 |
|  | MZ | 1 |  | 1 |  |  |
| 159 | WW | 1 |  |  |  | 3 |
|  | BR |  |  |  |  |  |
|  | RC |  |  |  |  |  |
|  | AP |  |  |  |  |  |
|  | MZ | 1 |  |  |  |  |
| 113 | WW | 1 |  |  |  | 1 |
|  | BR |  |  |  | 1 |  |
|  | RC |  |  |  |  |  |
|  | AP |  |  |  |  |  |
|  | MZ |  |  |  |  |  |
| 2 | WW | 2 | 1 |  | 2 | 3 |
|  | BR | 1 | 1 |  |  | 2 |
|  | RC | 2 |  |  |  | 2 |
|  | AP | 2 | 1 | 1 | 1 | 2 |
|  | MZ |  |  |  |  |  |

EXAMPLE 31

Intermediate Apple Retardant Test

Methodology

The variety of apples used in this test was Red Delicious and the growth stage at spray was 4 leaves or 5–10 cm high. The apples were grown in 4" pots in a mixture of JIP, loam and grit..(JIP is John Innes Potting compost). Compounds were applied at 1000 ppm and 4000 ppm respectively (1 kg and 4 kg ha$^{-1}$ at a field volume of 1000 l ha$^{-1}$) as an overall spray. This gives a foliar and root componet in the test, i.e. this test will detect the activity of both root and foliar acting compounds. The plants were assessed for height to apex at approximately 14–28 days after the treatment depending on the rate of growth. The results which are an average of 5 repliates are presented in Table VII. In each case the result for the 1000 ppm and 4000 ppm test for each compound is compared to the height of the formulation blank in that test, presented as a percentage reduction in height compared to the formulation blank.

TABLE VII

Percentage Reduction in Height of Apples
(Compared to formulation blank)

| COMPOUND NO. | Rate | |
|---|---|---|
|  | 1000 ppm | 4000 ppm |
| 1 | 43.1 | 58.5 |
| 2 | 17.9 | 32.2 |
| 17 | 35.2 | 62.9 |
| 51B | 42.4 | 57.2 |
| 51A | 36.8 | 58.9 |
| 23A | 33.8 | 57.5 |
| 19 | 30.0 | 61.3 |
| 142 | 29.6 | 62.6 |
| 121 | 12.1 | 52.4 |
| 131 | 6.4 | 54.7 |

TABLE VII-continued

Percentage Reduction in Height of Apples
(Compared to formulation blank)

| COMPOUND NO. | Rate | |
|---|---|---|
|  | 1000 ppm | 4000 ppm |
| 135 | 4.7 | 51.4 |

EXAMPLE 32

Intermediate Barley Retardant Test

Methodology

The variety of spring barley used in this test was Atem and the growth stage at spray was 3 leaves. The plants were grown in 4" pots in JIP. Compounds were applied at 1000 ppm and 4000 ppm respectively (1 kg and 4 kg ha$^{-1}$ at a field volume of 1000 l ha$^{-1}$) as an overall spray. This gives a foliar and root component in the test, i.e. this test will detect the activity of both root and foliar acting compounds. The plants were assessed for height to topmost ligule at approximately 28 days after treatment. The results which are an average of 5 replica are presented in Table VIII. In each case the result for the 1000 ppm and 4000 ppm test for each compound is compared to the height of the formulation blank in that test, presented as a percentage reduction in height compared to the formulation blank.

TABLE VIII

Percentage Reduction in Height of Spring Barley
(Compared to formulation blank)

| COMPOUND NO. | Rate | |
|---|---|---|
|  | 1000 ppm | 4000 ppm |
| 1 | 21.9 | 42.0 |
| 8 | 15.6 | 54.1 |
| 2 | 44.9 | 77.8 |
| 7 | 24.8 | 41.8 |
| 10 | 7.5 | 35.5 |
| 51B | 23.6 | 61.3 |
| 51A | 13.1 | 38.5 |
| 23A | 9.6 | 35.6 |
| 121 | 0 | 48.8 |

EXAMPLE 33

Intermediate Rice Retardant Test

Methodology

The variety of rice used in this test was Ishikari and growth stage at spray was 3–4 leaves. The rice was grown in 4" 'paddy' pots in a mixture of JIP, loam and grit. The roots and bottom of the stems are immersed in water under conditions corresponding to those in paddy fields. The compounds were applied at 1000 ppm and 4000 ppm respectively (1 kg and 4 kg ha$^{-1}$ at a field volume of 1000 l ha$^{-1}$) as an overall spray. This gives a foliar and root component in the test, i.e. this test will detect the activity of both root and foliar acting compounds. The plants were assessed for height to top-most ligule at approximately 28 days after treatment. The results which are an average of 5 replicates are presented in Table IX. In each case the result for the 1000 ppm and 4000 ppm test for each compound is compared to the height of the formulation blank in that test, presented as a percentage reduction in height compared to the formulation blank.

TABLE IX

| | Percentage Reduction in Height of Rice (Compared to formulation blank) | |
| --- | --- | --- |
| | Rate | |
| COMPOUND NO. | 1000 ppm | 4000 ppm |
| 1 | 10.7 | 37.0 |
| 7 | 7.9 | 36.1 |
| 10 | 34.0 | 59.3 |
| 51B | 38.0 | 57.8 |
| 142 | 16.7 | 46.3 |
| 119 | 24.2 | 48.3 |
| 120 | 28.5 | 48.7 |
| 131 | 25.6 | 59.3 |
| 132 | 26.4 | 48.3 |
| 135 | 18.1 | 44.6 |

We claim:

1. A compound having the general formula:

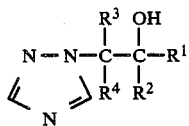

and stereoisomers thereof, wherein $R^1$ is tertiary butyl, optionally substituted with halogen; $R^2$ is selected from the group consisting of —C≡C—X, —CH=CH—X and —CH$_2$—CH$_2$—X where —X is alkyl containing from 3 to 5 carbon atoms and optionally substituted by halogen; $R^3$ is hydrogen and $R^4$ is alkyl of up to 4 carbon atoms and esters, acid-addition salts and metal complexes thereof.

2. A compound according to claim 1 wherein $R^1$ is tertiary butyl of 2-fluoro-1,1-dimethylethyl.

3. A compound according to claim 1 wherein $R^4$ is methyl ethyl.

4. The compound

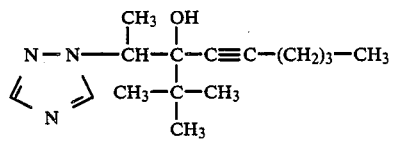

5. A plant growth regulating composition comprising an effective amount of a compound according to claim 1, or a salt, metal complex, or ester thereof; and a carrier or diluent.

6. A method of regulating plant growth, which comprises applying to the plant, to the seed of a plant or to the locus of the plant or seed an effective amount of a compound according to claim 1 or a salt, metal complex, or ester thereof.

* * * * *